US012666184B2

(12) United States Patent
Jumbe et al.

(10) Patent No.: US 12,666,184 B2
(45) Date of Patent: Jun. 23, 2026

(54) SECURE IDENTIFICATION METHODS AND SYSTEMS

(71) Applicants:LEVEL 42 AI INC., Mountain View, CA (US); Nelson L. Jumbe, Mountain View, CA (US); Michael Morimoto, Mountain View, CA (US); Andreas Schuh, Mountain View, CA (US); Todd Rooke, Mountain View, CA (US); Krzysztof Krawiec, Mountain View, CA (US); Kevin Hammond, Mountain View, CA (US)

(72) Inventors: Nelson L. Jumbe, Mountain View, CA (US); Michael Morimoto, Mountain View, CA (US); Andreas Schuh, Mountain View, CA (US); Todd Rooke, Mountain View, CA (US); Krzysztof Krawiec, Mountain View, CA (US); Kevin Hammond, Mountain View, CA (US)

( * ) Notice: Subject to any disclaimer, the term of this patent is extended or adjusted under 35 U.S.C. 154(b) by 387 days.

(21) Appl. No.: 18/043,986

(22) PCT Filed: Sep. 3, 2021

(86) PCT No.: PCT/US2021/049161
§ 371 (c)(1),
(2) Date: Mar. 3, 2023

(87) PCT Pub. No.: WO2022/051679
PCT Pub. Date: Mar. 10, 2022

(65) Prior Publication Data
US 2023/0328417 A1      Oct. 12, 2023

Related U.S. Application Data

(63) Continuation of application No. 17/096,806, filed on Nov. 12, 2020, now Pat. No. 11,240,579, and a
(Continued)

(30) Foreign Application Priority Data

May 8, 2021     (WO) .................. PCT/IB2021/053919

(51) Int. Cl.
*H04R 1/04*          (2006.01)
*A61B 5/00*          (2006.01)
(Continued)

(52) U.S. Cl.
CPC ............. *H04R 1/04* (2013.01); *A61B 5/0002* (2013.01); *A61B 5/0531* (2013.01); *A61B 5/277* (2021.01);
(Continued)

(58) Field of Classification Search
None
See application file for complete search history.

(56) References Cited

U.S. PATENT DOCUMENTS 10,231,651 B2    3/2019  Deng et al.
11,722,571 B1 *  8/2023  Chenier .................. G10L 17/22
                                                    709/224
(Continued)

OTHER PUBLICATIONS

International Search Report and Written opinion issued in corresponding application No. PCT/US2021/049161 on Feb. 8, 2022.
(Continued)

*Primary Examiner* — Jeffrey R Swearingen
(74) *Attorney, Agent, or Firm* — BCF LLP

(57)          ABSTRACT
There is disclosed a method of and a system for generating a unique identifier for a subject. Biometric data related to the
(Continued)

subject is received. Identification markers from the biometric data are extracted. The unique identifier is generated from the extracted identification markers by identifying a given domain specific feature which has a predetermined identity compared to other domain specific features. Feature values are generated based on the biometric data and stored in a user profile of the subject.

18 Claims, 15 Drawing Sheets

Related U.S. Application Data continuation of application No. PCT/US2021/046566, filed on Aug. 18, 2021.

(60) Provisional application No. 63/075,059, filed on Sep. 4, 2020.

(51) Int. Cl.

| | |
|---|---|
| *A61B 5/0531* | (2021.01) |
| *A61B 5/277* | (2021.01) |
| *A61B 5/318* | (2021.01) |
| *A61B 7/04* | (2006.01) |
| *A61B 8/00* | (2006.01) |
| *G01P 1/00* | (2006.01) |
| *G01P 15/08* | (2006.01) |
| *G10L 25/66* | (2013.01) |
| *H04R 1/46* | (2006.01) |
| *H04R 9/02* | (2006.01) |
| *H04R 9/04* | (2006.01) |
| *H04R 9/08* | (2006.01) |

(52) U.S. Cl.
CPC .............. *A61B 5/318* (2021.01); *A61B 5/412* (2013.01); *A61B 5/7267* (2013.01); *A61B 7/04* (2013.01); *A61B 8/488* (2013.01); *G01P 1/00* (2013.01); *G01P 15/08* (2013.01); *G10L 25/66* (2013.01); *H04R 1/46* (2013.01); *H04R 9/025* (2013.01); *H04R 9/045* (2013.01); *H04R 9/08* (2013.01); *A61B 2560/0214* (2013.01); *A61B 2560/0252* (2013.01); *A61B 2560/0257* (2013.01); *A61B 2560/0431* (2013.01); *A61B 2560/0443* (2013.01); *A61B 2562/0204* (2013.01); *A61B 2562/0219* (2013.01)

(56) References Cited

U.S. PATENT DOCUMENTS

| | | | |
|---|---|---|---|
| 2011/0208781 | A1 | 8/2011 | Liu et al. |
| 2012/0138680 | A1 | 6/2012 | Litz et al. |
| 2017/0141920 | A1 | 5/2017 | Herder, III et al. |
| 2017/0180336 | A1 | 6/2017 | Josephson et al. |
| 2017/0264608 | A1 | 9/2017 | Moore et al. |
| 2017/0366543 | A1 | 12/2017 | Wang et al. |
| 2019/0140833 | A1 | 5/2019 | Grajek et al. |
| 2020/0356338 | A1* | 11/2020 | Shoop .................... H04N 21/47 |
| 2020/0364428 | A1* | 11/2020 | Azanza Ladrón ...... G06F 21/36 |
| 2023/0306783 | A1* | 9/2023 | Irie ...................... G06V 40/172 |

OTHER PUBLICATIONS

Thomas et al., "Utilizing individual alpha frequency and delta band power in EEG based biometric recognition", 2016 IEEE International Conference on Systems, Man and Cybernetics, First retrieved on Jan. 24, 2022, https://ieeexplore.ieee.org/abstract/document/7844987.

Ambadiyil et al., "Biometric based Unique ID Generation and One to One Verification for Security Documents", Sciencedirect Procedia Computer Science 46 (2015), First retrieved on Jan. 24, 2022.

* cited by examiner

Figure 15:
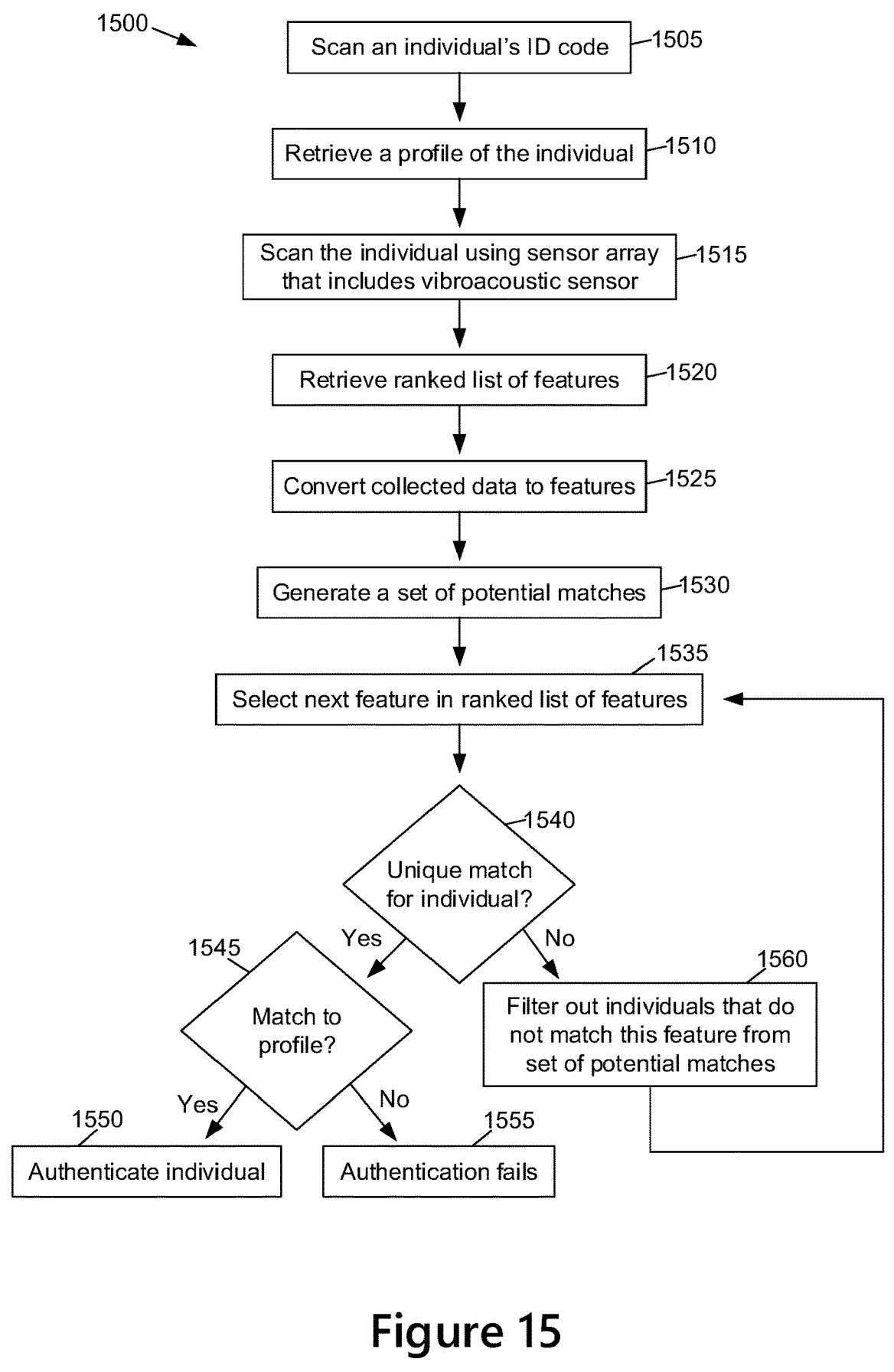

1500

Scan an individual's ID code —1505

Retrieve a profile of the individual —1510

Scan the individual using sensor array
that includes vibroacoustic sensor —1515

Retrieve ranked list of features —1520

Convert collected data to features —1525

Generate a set of potential matches —1530

1535

Select next feature in ranked list of features

1540

Unique match
for individual?

Yes          No

1545

Match to
profile?

Yes          No

1560

Filter out individuals that do
not match this feature from
set of potential matches 1550                    1555

Authenticate individual          Authentication fails

SECURE IDENTIFICATION METHODS AND SYSTEMS

CROSS-REFERENCE TO RELATED APPLICATIONS

This application claims the benefit of U.S. Provisional Patent Application No. 63/075,059, filed Sep. 4, 2020, U.S. Provisional Patent Application No. 63/075,056, filed Sep. 4, 2020, U.S. patent application Ser. No. 17/096,806, filed Nov. 12, 2020, International Patent Application No. PCT/IB32021/053919, filed May 8, 2021, and International Patent Application No. PCT/US2021/046566, filed Aug. 18, 2021, each of which is incorporated by reference herein in its entirety. This application is related to a concurrently filed PCT application entitled "NON-CONTACT SENSOR SYSTEMS AND METHODS", which is incorporated by reference herein in its entirety.

FIELD

This technology relates to trusted IoT hardware and software framework for the generation of unforgeable identification credentials and use of these unforgeable positive identification trusted credentials.

BACKGROUND

The U.S. Government Accountability Office (GAO) has designated the Centers for Medicare and Medicaid Services (CMS) as high-risk programs, in part due to their susceptibility to improper payments estimated to be about >$50 billion year on year. Improper payments have many causes, such as submissions of duplicate claims or fraud, waste, and abuse. Importantly, the post-COVID-19 "next normal" requires rethinking of Health and Safety whereby, "safety" now includes disease, food supply chain and travel (import/export), health screening/diagnosis and contact tracing, etc., (which all have secure identity underpinnings).

The present disclosure pertains to novel solutions for trusted personal identification systems. In particular, to a system for the generation of unforgeable biometric physiology identification credentials and use of these unforgeable identification credentials for safe and secure transfer of services. Unforgeable identity may be ephemeral or persistent. Unforgeable identity may be local or distributed. Unforgeable identity may be closed/private or open/public. Unforgeable identity may be online or offline. Unforgeable identity may be at an individual (atom) or crowd/population (ecology) level.

Biometric systems operate on behavioral and physiological biometric data to identify a person. Common behavioral biometric parameters are signature, gait, speech and keystroke, these parameters change with age and environment. Additional physiological characteristics such as face, fingerprint, palm print and iris largely remain unchanged throughout the life time of a person. The biometric system operates as verification mode or identification mode depending on the requirement of an application. The verification mode validates a person's identity by comparing captured biometric data with ready-made template. The identification mode recognizes a person's identity by performing matches against multiple fingerprint biometric templates. Fingerprints are widely used in daily life for more than 100 years due to its feasibility, distinctiveness, permanence, accuracy, reliability, and acceptability.

Separately, over the past decade, there has been significant innovation in distributed ledger technologies (DLTs). Blockchain technology, a form of DLT, allows a network of independent peer nodes to maintain a consistent view of shared state through consensus, thus enabling decentralized trust. This technology is the basis for well-known decentralized permissionless networks such as Bitcoin [Satoshi Nakamoto. 2009. Bitcoin: A peer-to-peer electronic cash system. http://bitcoin.org/bitcoin.pdf. (2009)] and Ethereum [Ethereum Foundation. 2019. Ethereum. (2019). https://www.ethereum.org/]. However, applications addressing enterprise use cases impose additional requirements such as scalability, privacy, confidentiality, interoperability, and auditability. These requirements have led to the development of multiple competing permissioned blockchain networks. Today, there is a wide spectrum of protocol and platform choices for building permissioned networks.

Additionally, over the past several years Decentralized Identity (DID) technology has also seen significant innovation and standardization. With over fifty organizations participating in the W3C Decentralized Identifier working group; including Microsoft, Intel, Google, Lenovo, and MITRE [W3C (2021) https://www.w3.org/groups/wg/did/ipr]. Decentralized identifiers (DIDs) are a new type of identifier that enables verifiable, decentralized digital identity. Microsoft is a founding member of the Decentralized Identity Foundation (DIF) and announced in 2019 it was developing ION (Identity Overlay Network). Since then, the DIF has developed ION based on SideTree, a distributed Layer 2 network, that anchors the hashed ID's of its users on the Bitcoin public blockchain, and maintains the encrypted identity data within ION's distributed network. In 2021, v1 of ION was launched as the first open, public, permissionless Layer 2 Decentralized Identifier network that runs atop the Bitcoin blockchain [https://github.com/decentralized-identity/ion].

SUMMARY OF THE DISCLOSURE

Aspects of the present disclosure contemplate end to end unforgeable Uniform Biometric Identifier and Uniform Biometric Locator systems, which are implemented separately and are interoperable with existing distributed ledger technologies. This implemented technology can; 1) generate a "verifiable credential", 2) prove "access control" attributes related to said "verifiable credential", 3) deliver "conditional access" capability by extending "verifiable credential", and "access control" primitives with "state and status biometrics" through its sensor fusion technology.

In certain aspects, there is provided a Decentralized Identifier technology, referred to herein as uDIDt.

In certain aspects, there is provided methods and systems for generating a unique verifiable credential identifier of a person, referred to herein as uDIDt-VeCx.

In certain aspects, there is provided methods and systems for using the uDIDt-VeCx for proof of "access control" based on "verifiable credential" attributes in secure transactions. Transactions may include any type of transaction such as a commercial transaction, a security clearance, machinery or autonomous vehicle, and the like.

In certain embodiments, methods and systems of the present technology may be used for "access control"/"conditional access" by extending "verifiable credentials" for health/travel passports during pandemic or disaster emergencies.

In certain embodiments, methods and systems of the present technology may be used for current health state and status confirmation at ports-of-entry.

In certain embodiments, methods and systems of the present technology may be used for generating a "verifiable credential" or "keycard" for entry.

In certain embodiments, the novel biosignature unforgeable globally unique identifier (uDIDt-VeCx) is based on an integration of central nervous system and autonomic nervous system biofield signatures that are immutable and valid only during the time that a person is alive (also referred to herein as "biosignature"). The biosignature may include data relating to any physiological parameter of the person (see Table 1 for examples).

All current attempts at unique identifiers relieve the individual of any control on how they are identified. Current unique identifiers are issued by external authorities that decide who or what they identify and when they can be revoked. They are useful only in certain contexts and recognized only by certain bodies (not of the individual's choosing). They may disappear or cease to be valid with the failure of an organization. They may unnecessarily reveal personal information. And in many cases, they can be fraudulently replicated and asserted by a malicious third-party ("identity theft").

The unique Decentralized Identifier technology (uDIDt) defined in this disclosure is a new type of globally unique identifier designed to enable individuals and organizations to generate their own identifiers (uDIDt-VeCx) using systems they trust, and to prove control of those identifiers (authenticate) using cryptographic proofs (eg., digital signatures, privacy-preserving biometric protocols, etc).

The current technology may comprise embodiments disclosed in the U.S. patent application 63/067,179 filed Aug. 18, 2020, the contents of which are herein incorporated by reference.

In the context of the present specification, unless expressly provided otherwise, a computer system may refer, but is not limited to, an "electronic device", an "operation system", a "system", a "computer-based system", a "controller unit", a "control device" and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid state-drives, and tape drives.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

Embodiments of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of embodiments of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where:

FIG. 10 illustrates certain embodiments of the methods and systems of the present technology in which additional data is obtained from the subject relating to an event, and labelled with the generated unique identifier. This can be used for anonymized feedback. For example, the obtained additional data may be physiological data from which an emotional or cognitive state of the subject can be derived. The event can be a show, a talk, a presentation, teaching, an activity such as driving a vehicle, operating machinery, and the like.

FIG. 15 is a flow diagram of a method for authenticating an individual in accordance with various embodiments of the present technology.

Figure 1:
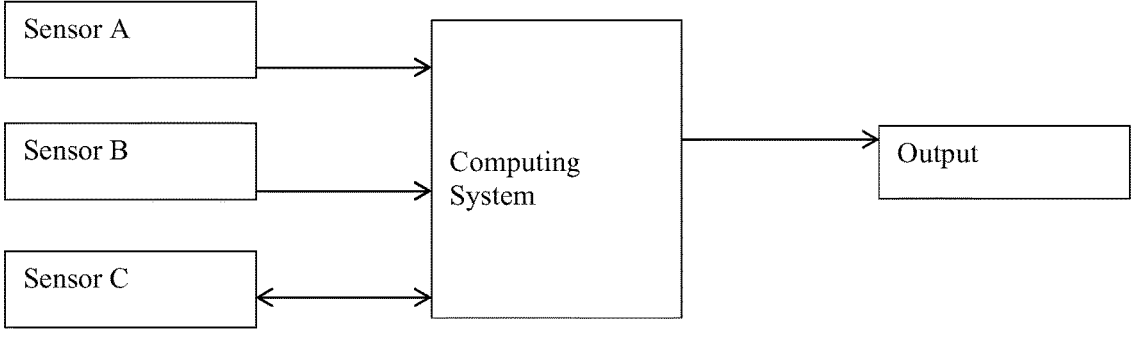
FIG. 1 is a block diagram of a system in accordance with various embodiments of the present technology.

It should be noted that, unless otherwise explicitly specified herein, the drawings are not to scale.

DETAILED DESCRIPTION

In certain embodiments, the Decentralized Identifiers (uDIDt-VeCx) may be a component of larger systems Verifiable Credentials ecosystems [VeCx]. Design goals for the uDIDt-VeCx may include but are not limited to the following.

In one embodiment, the current disclosure provides methods and systems that achieve the goal of decentralization in order to eliminate the requirement for centralized authorities or prevent single point failure in identifier management, including the registration of globally unique identifiers, public verification keys, service endpoints, and other metadata.

In another embodiment, the current disclosure provides methods and systems that achieve the goal of control, giving individuals, groups, communities, etc., i.e. "ecologies", both human and non-human entities, the power to directly control their digital identifiers.

In still another embodiment, the current disclosure provides methods and systems that achieve the goal of privacy, enabling entities to control the privacy of their information, including minimal, selective, and progressive disclosure of attributes or other data.

In one embodiment, the current disclosure provides methods and systems that achieve the goal of security, enabling sufficient security for requesting parties to depend on uDIDt-VeCx documents for their required level of assurance.

In another embodiment, the current disclosure provides methods and systems that achieve the goal of proof-basis, enabling uDIDt-VeCx controllers to provide cryptographic proof when interacting with other entities.

In still another embodiment, the current disclosure provides methods and systems that achieve the goal of discoverability, making it possible for entities to discover uDIDt-VeCx for other entities, to learn more about or interact with those entities.

In one embodiment, the current disclosure provides methods and systems that achieve the goal of interoperability, using interoperable standards so uDIDt-VeCx infrastructure can make use of existing tools and software libraries designed for interoperability.

In another embodiment, the current disclosure provides methods and systems that achieve the goal of Portability, being system- and network-independent and enabling entities to use their digital identifiers with any system that supports uDIDt-VeCx and uDIDt-VeCx methods.

In still another embodiment, the current disclosure provides methods and systems that achieve the goal of simplicity, favoring a reduced set of simple features to make the technology easier to understand, implement, and deploy.

In one embodiment, the current disclosure provides methods and systems that achieve the goal of extensibility, where possible, enabling extensibility provided it does not greatly hinder interoperability, portability, or simplicity.

Because unforgeable living biometric/biosignatures/biofields underlie the generation and assertion of these identifiers, each individual is themselves the unique immutable uDIDt-VeCx from which many child uDIDts and VeCx may be spawned to satisfy any need and to respect desired separation of identities, personas, and contexts. In addition, subsequent uDIDts and VeCx scope and the use of these identifiers can be tailored appropriately for different contexts. In this way an individual can interact with other people, communities, institutions or systems that require trusted identification while maintaining control over how much personal or private data can and should be revealed, and without depending on a central authority to guarantee the continued existence of the identifier. Further, these unforgeable biometric/biosignatures/biofields also provide the behavioral and contextual information required for use in adaptive access control.

Thus, in certain embodiments, the present disclosure provides for methods and systems for cryptographically encoding specific combinations and subsets of biometric, biosignature, or biofield data to furnish distributed, unforgeable, and selectively non-deanonymizable personal or ecological identifiers.

In still another embodiment, the level of deanonymization can be selected from the individual level up through an arbitrarily large ecology (defined sub-population).

The use of intrinsic physical and behavioral traits of a human being to uniquely recognize an individual is called as biometrics. Biometric methods generally use a part of human body to identify a person and they are highly accurate. The biometric traits of an individual obtained must be transferred, stored, and retrieved in some way to verify the identity of the individual when required. Computer chips and RFID tags have been used for storing biometric information. For example, most countries have electronic passports containing an electronic chip with biometric information of the individual. Developing such a document with an RFID tag is a very complex and costly process. Also, the lifetimes of such devices are very limited. Hence development of new cost-effective methods having long lifetime for capturing, transferring, storing, and retrieving the biometric information is a critical technological challenge. Compared to computer chips and RFID tags, data hiding technologies like Quick Response (QR) code are much cheaper and do not require specialized hardware for retrieving data. QR codes are inexpensive, and they are traditionally passive read-only elements whose content cannot be altered. Decoding of the QR code can be done by many low-cost devices, including bring your own smart phones. As QR Code has high capacity, all the standardized features extracted from the uDIDt-VeCx could be encoded in it. It can be read from any direction and standard encryption techniques can be applied to the QR code to make it even more secure. We propose a novel technique for the development of a unique uDIDt-VeCx in the form of a QR (Quick Response) code by extracting the standardized feature based on the core points of unforgeable living biometric/biosignatures/biofields including facial/iris and fingerprints of an individual. The composite biosignature is converted to data hiding technologies like barcode, which use cross-frequency coupling and cross-phase signal coupling methods to classify the biosignatures. Then the biosignatures are further sub-classified and are converted into alphanumeric codes and then to corresponding barcodes.

System

In certain aspects, there is provided a system for generating a unique identifier for a subject. In certain embodiments, the unique identifier is based on biometric data of the subject.

It is to be expressly understood that the system is merely an illustrative implementation of the present technology. Thus, the description thereof that follows is intended to be only a description of illustrative examples of the present technology. This description is not intended to define the scope or set forth the bounds of the present technology. In some cases, what are believed to be helpful examples of modifications to the system may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art would understand, this is likely not the case. In addition, it is to be understood that the system 10 may provide in certain instances simple implementations of the present technology, and that where such is the case they have been presented in this manner as an aid to understanding. As persons skilled in the art would understand, various implementations of the present technology may be of a greater complexity.

In certain embodiments (FIG. 1), the system comprises one or more sensors for collecting data from the subject, in communication with a computing system for processing the data from the sensors, connected to an output system for providing an output of the processing of the data. The communication between the sensors and the computing system may be via a communication network. The communication network may be the Internet and/or an Intranet. Multiple embodiments of the communication network may be envisioned and will become apparent to the person skilled in the art of the present technology.

The computing system may implement any of the methods (described in further detail below) for processing the data received from the sensors. The computing system may include one or both of an MLA module and an MLA training module.

The computing system may comprise a computing environment which will be described below with reference to FIG. 2.

Computing Environment

Figure 2:
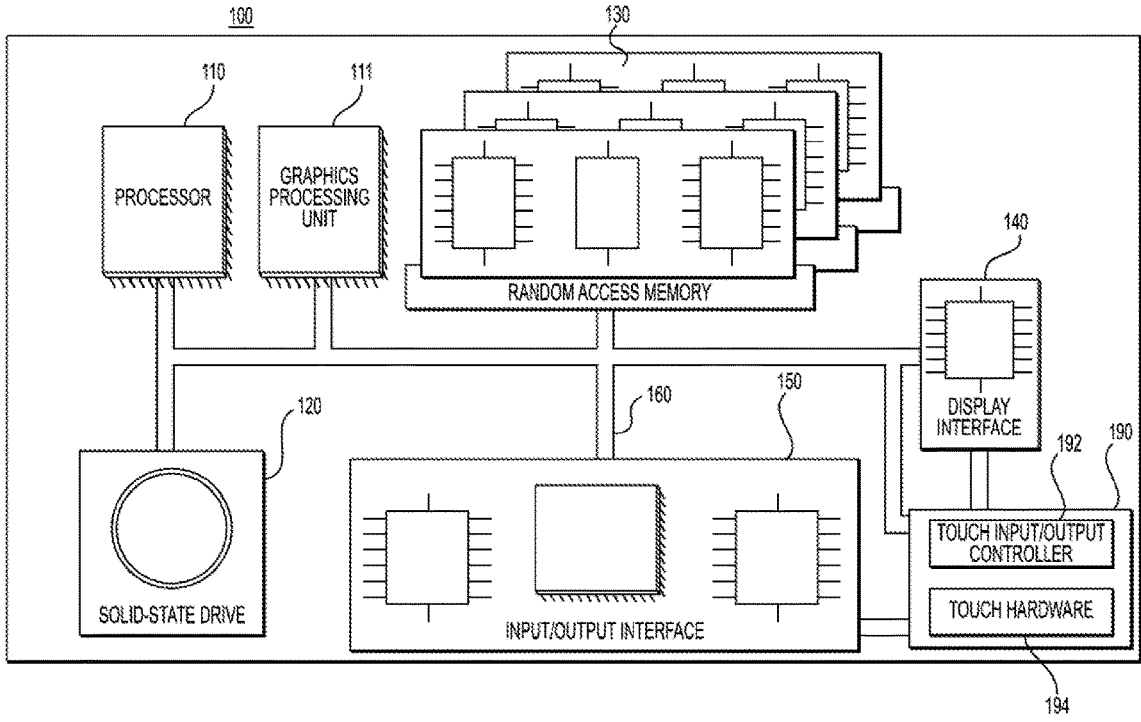
FIG. 2 is a block diagram of an example computing environment for implementing aspects of systems and methods in accordance with various embodiments of the present technology.
Figure 3:
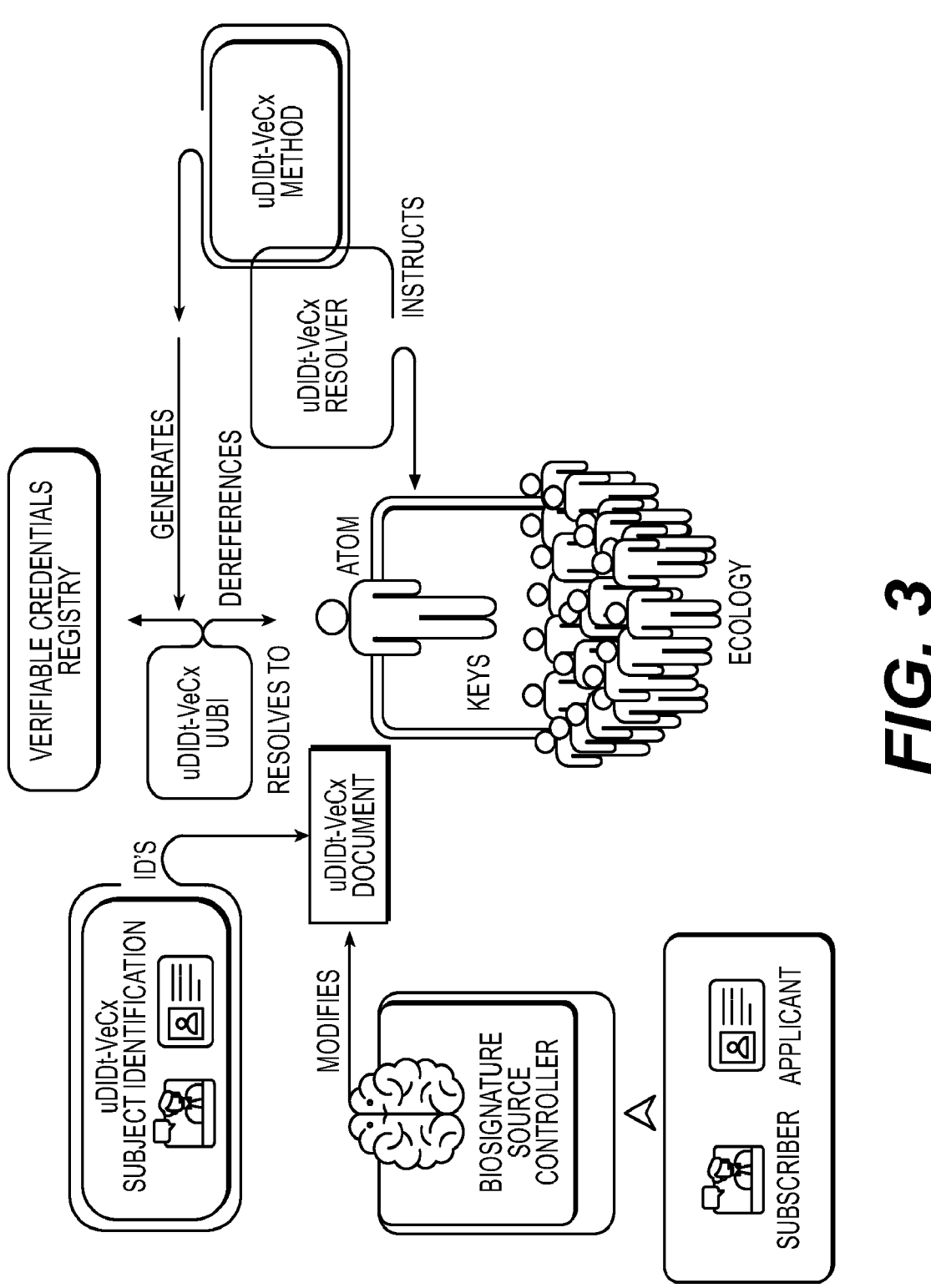
FIG. 3 is a schematic of a use of certain systems and methods of the present technology in accordance with various embodiments of the present technology.
Figure 4:
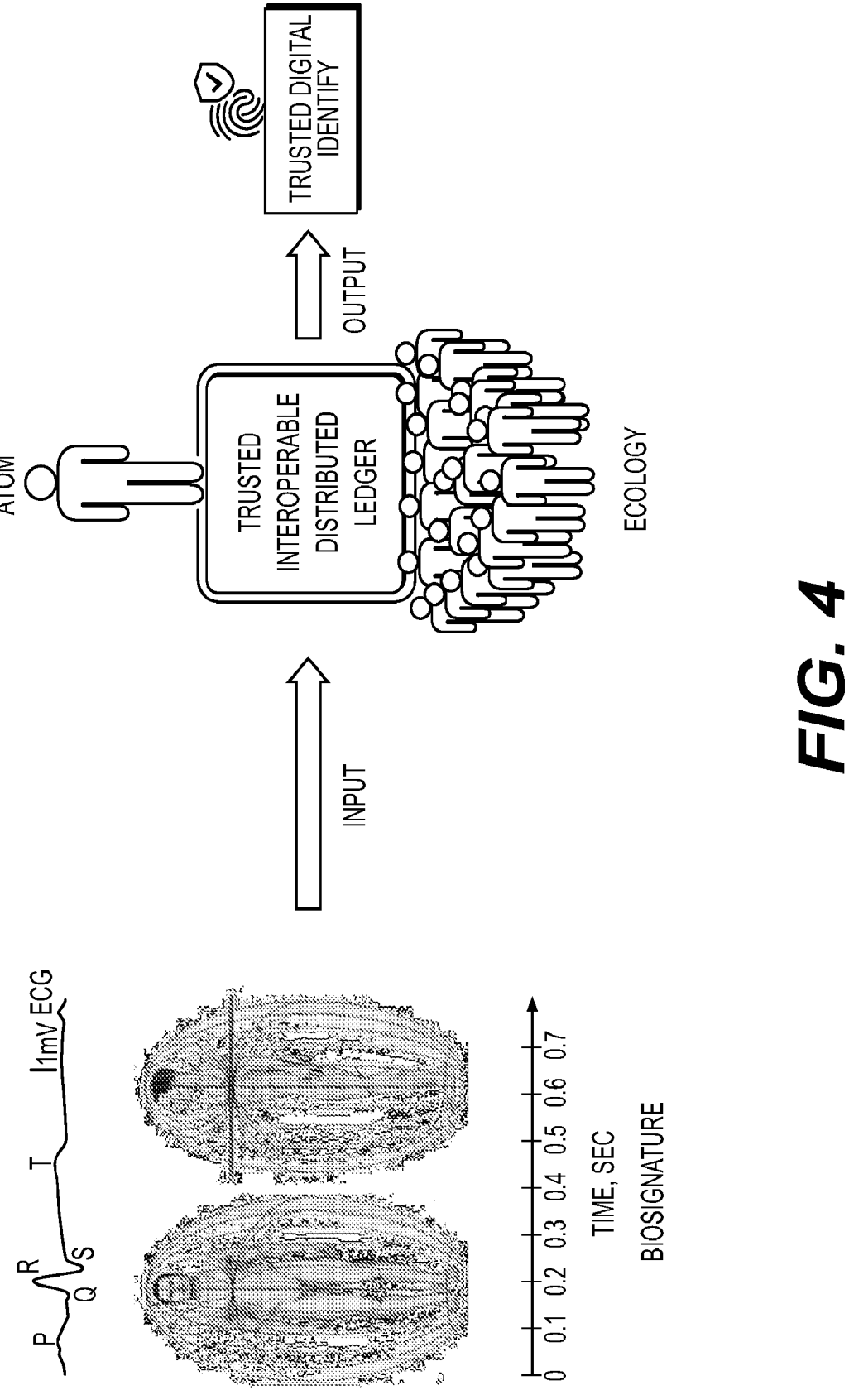
FIG. 4 is a schematic of a use of certain systems and methods of the present technology to generate a trusted digital identity (output) based on a biosignature input, for an individual (atom) or a group of individuals, in accordance with various embodiments of the present technology. The generated individual identifier can also be incorporated with an event information to generate a status identifier.
Figure 5:
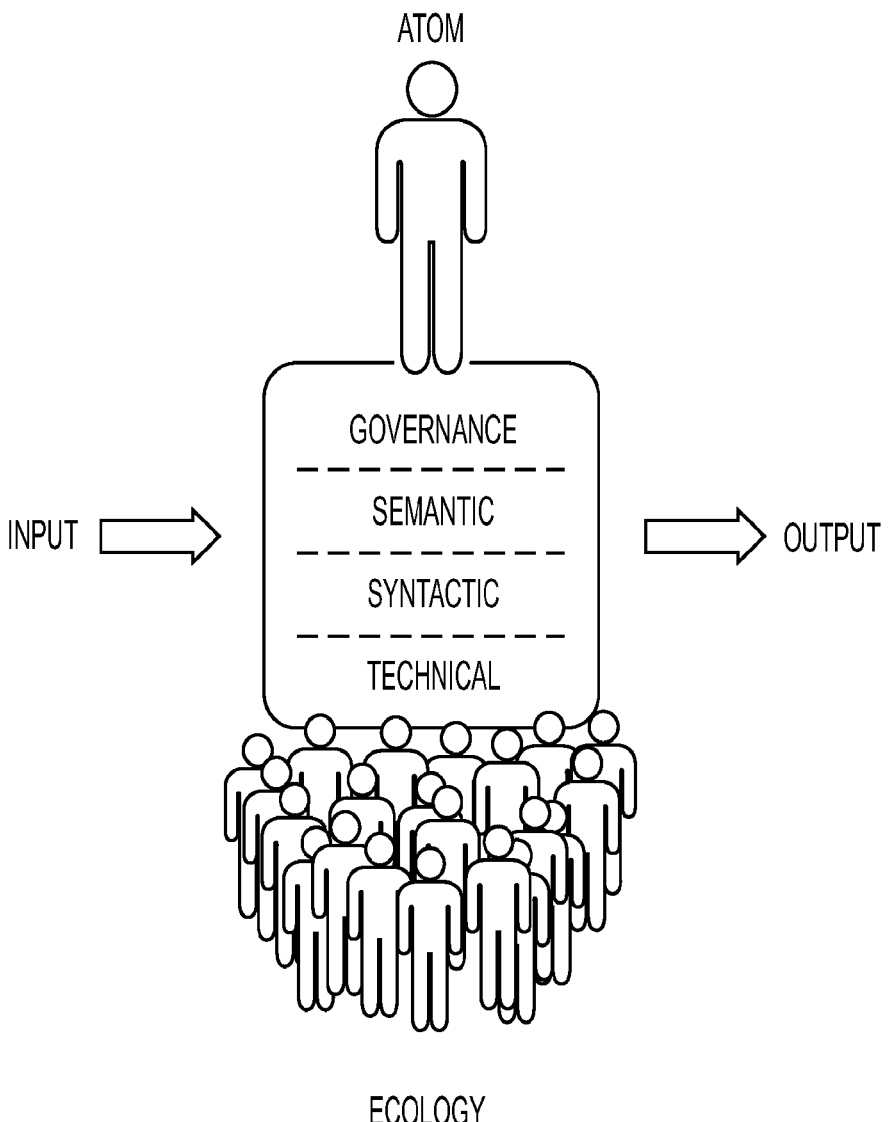
FIG. 5. illustrates a use of the generated unique identifier in generating a status identifier. The figure illustrates that abstraction can be performed at different levels for different use cases. For example, at a late-night show (the event), the generated unique identifier can be abstracted based on a governance of late-night shows determining the information to be included (e.g. where you were sitting, how much you paid for your ticket, what age group).
Figure 6:
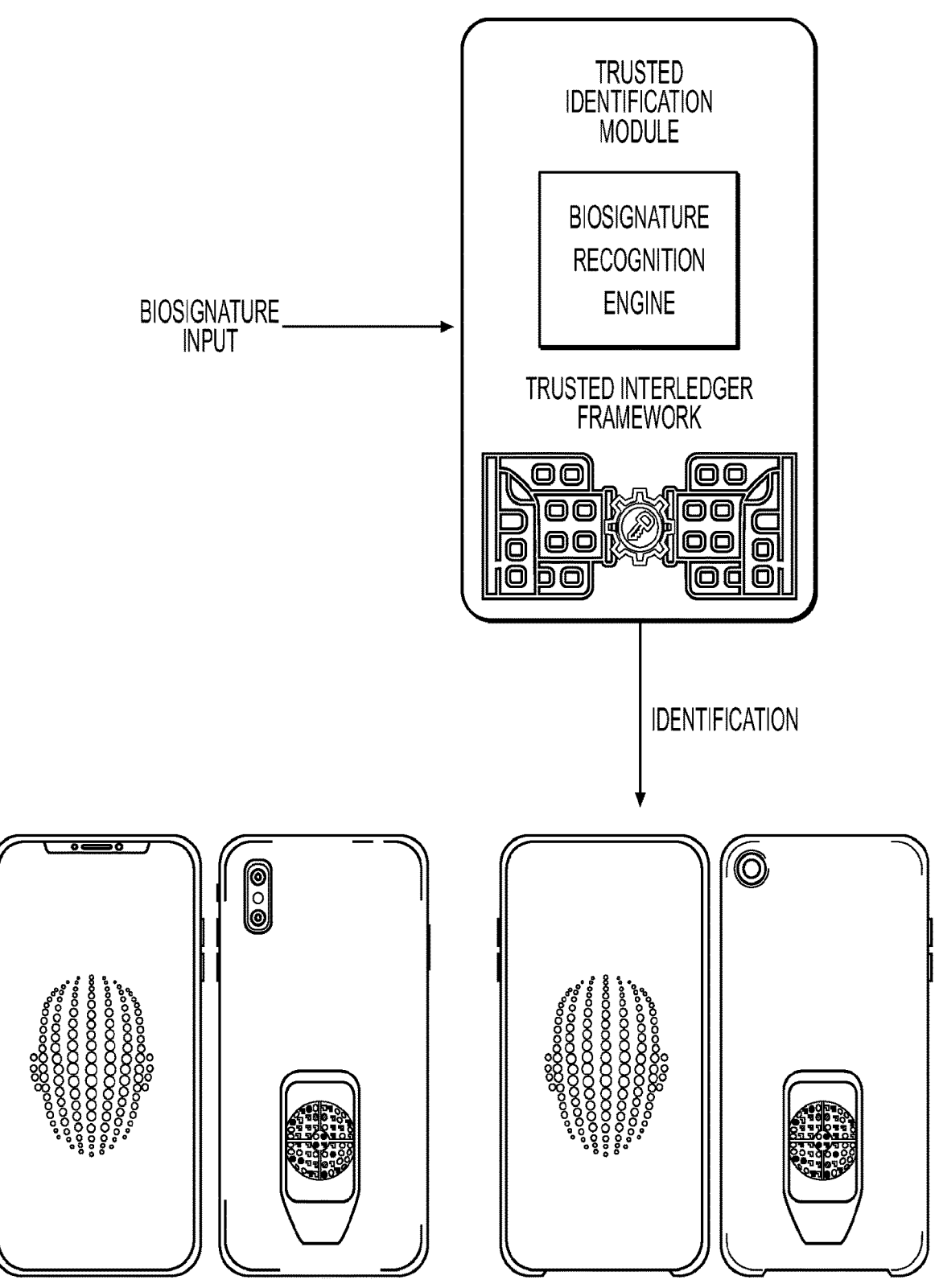
FIG. 6 is an illustration of FIG. 5 in more detail showing a distributed ledger in which a transaction is stored. This can add an extra level of security in certain use cases such as banking. A physical key may also be provided for verification and identification. In this way software and hardware components can be combined in certain embodiments.
Figure 7:
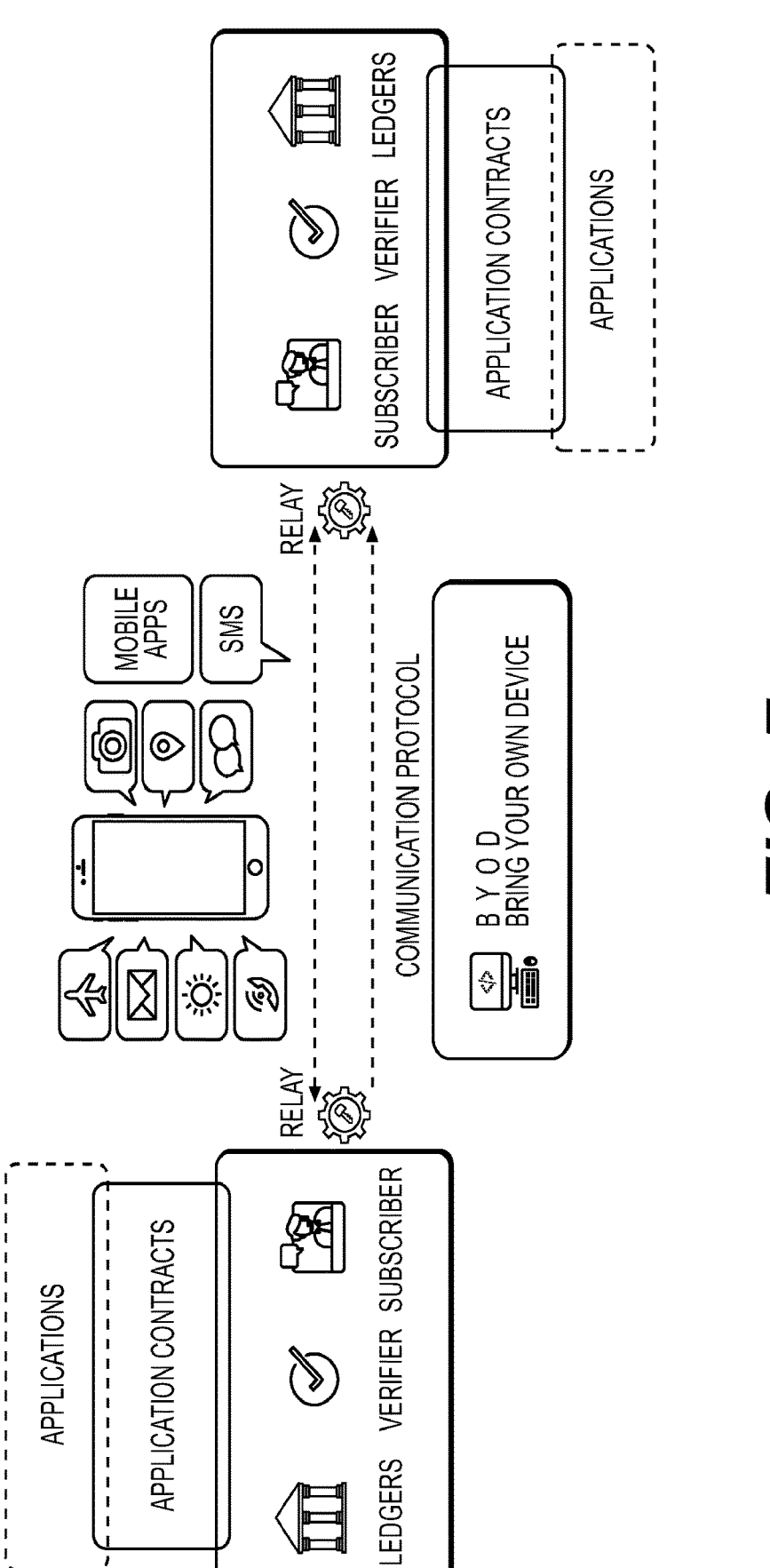
FIG. 7 illustrates a use of the generated unique identifier and is an expansion of FIG. 6.
Figure 8:
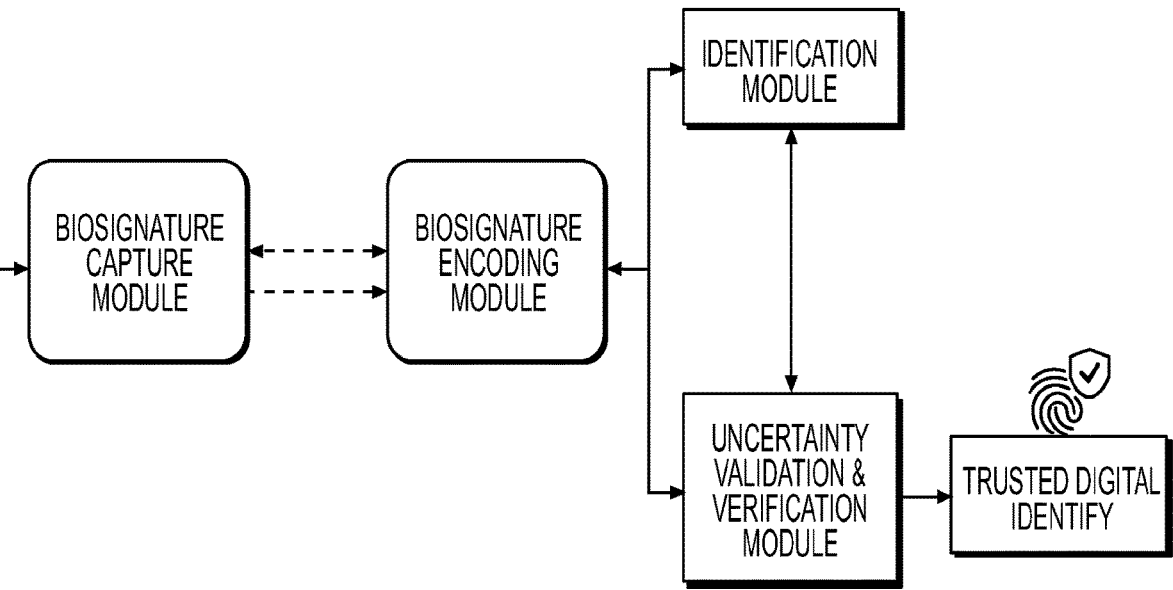
FIG. 8 is related to FIG. 4 and illustrates a concept of physiological drift which may create uncertainty. Once a drift threshold is crossed, methods of the present technology may comprise obtaining biometric data in a base-line update phase.
Figure 9:
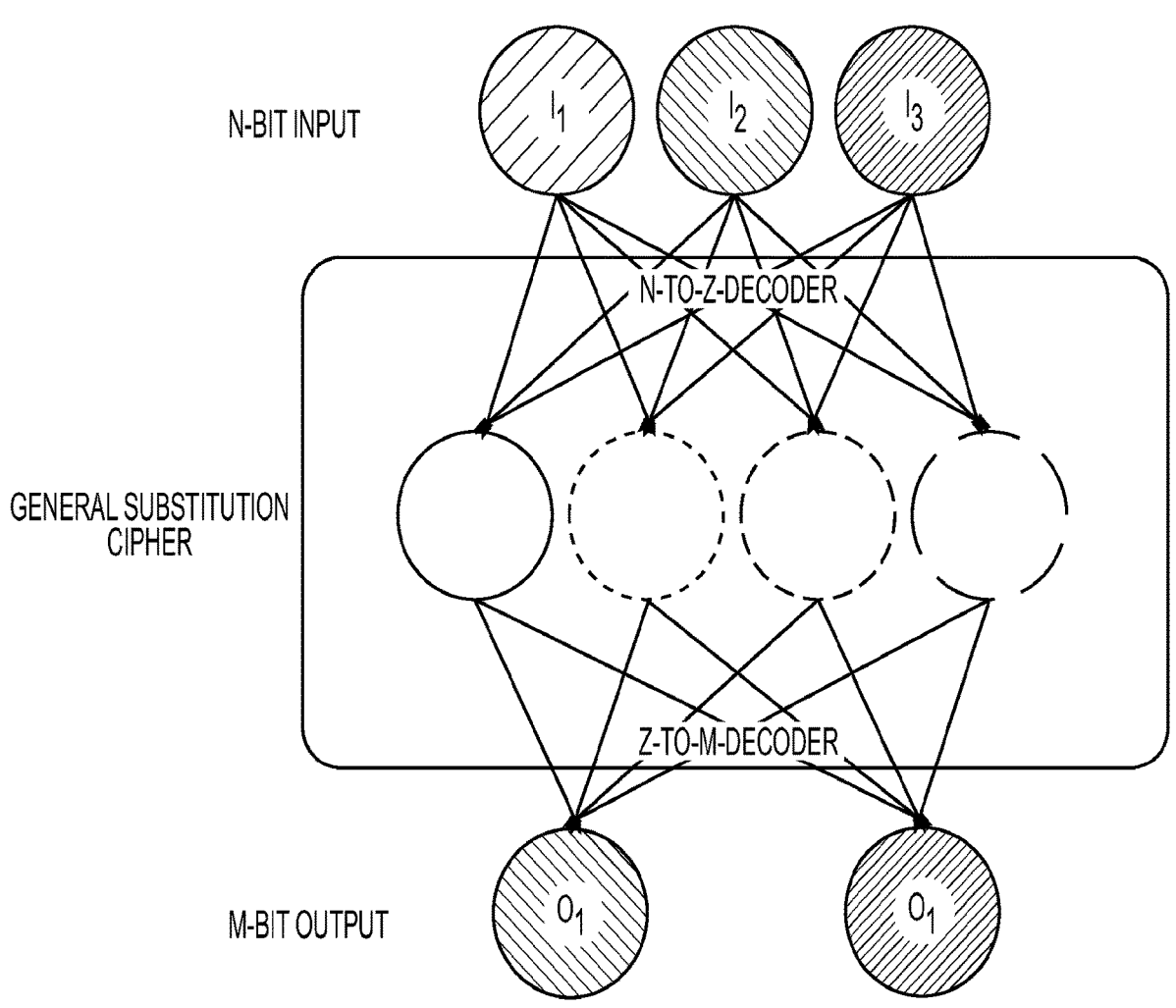
FIG. 9 illustrates the interoperability of the generated individual identifier, in certain embodiments with other identifiers from different digital encryption platforms which operate using different bits.
Figure 10:
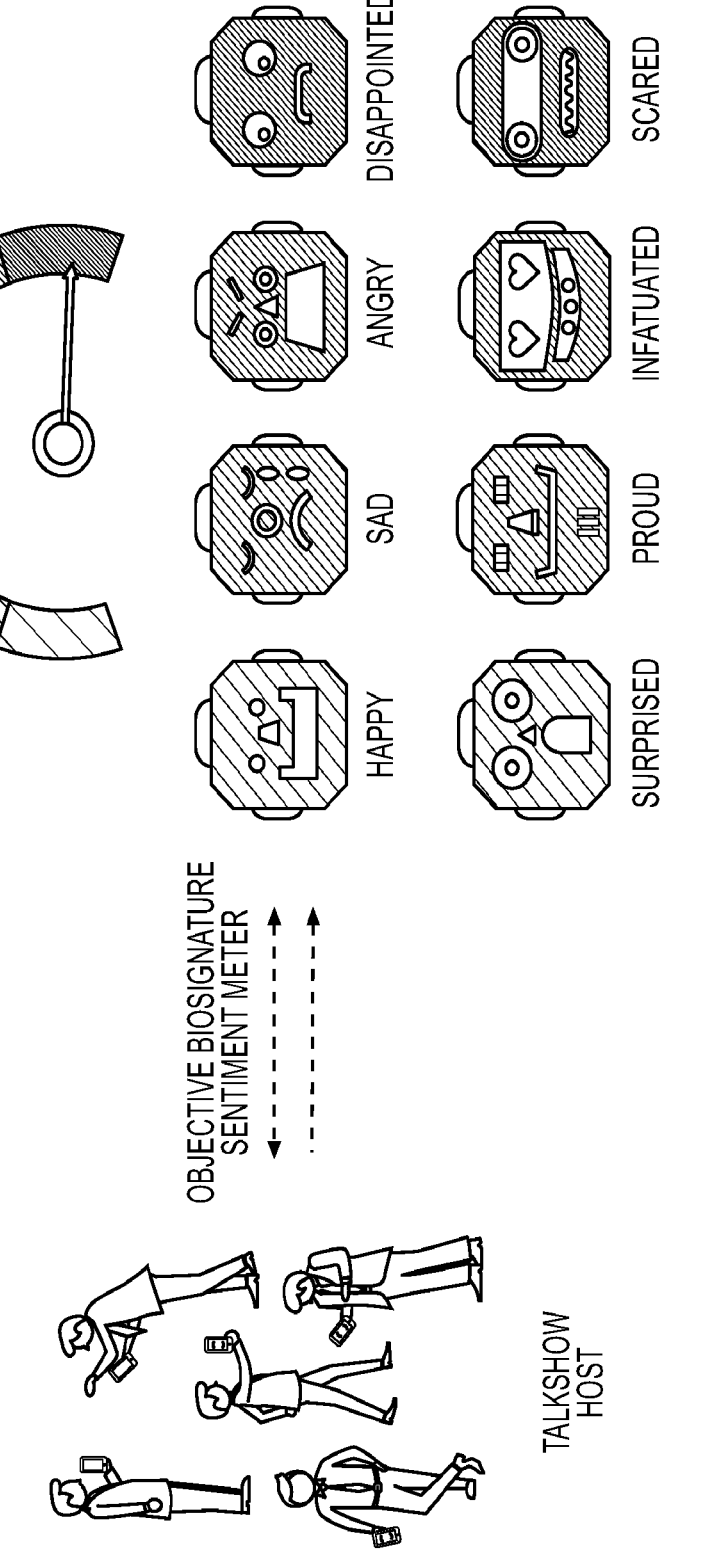
Figure 11:
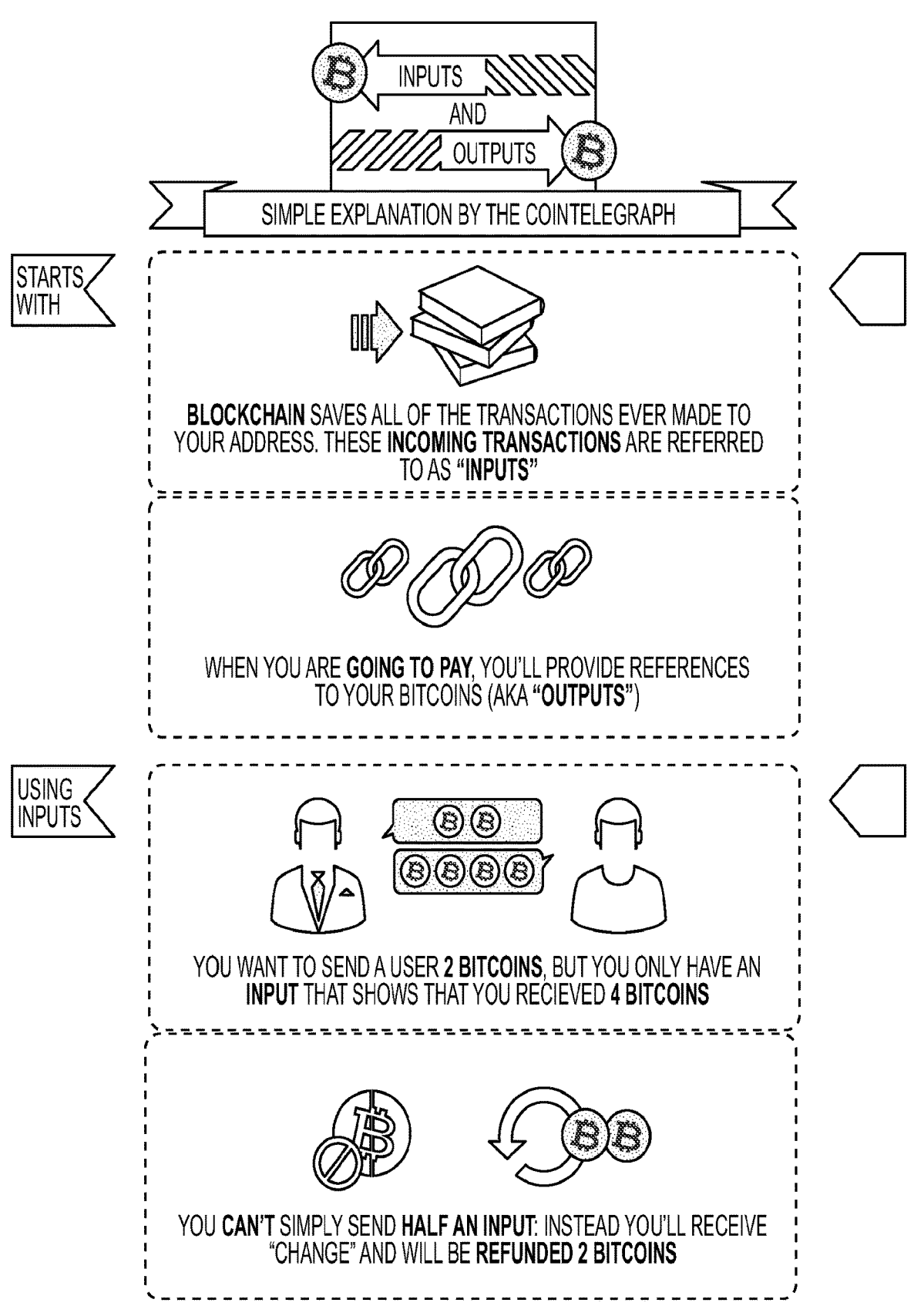
FIG. 11 illustrates certain embodiments of the methods and systems of the present technology in which the generated unique identifier can be used for transactions such as bitcoin transaction, and in certain embodiments providing a simpler transaction in terms of number of transactions and ledger size.
Figure 12:
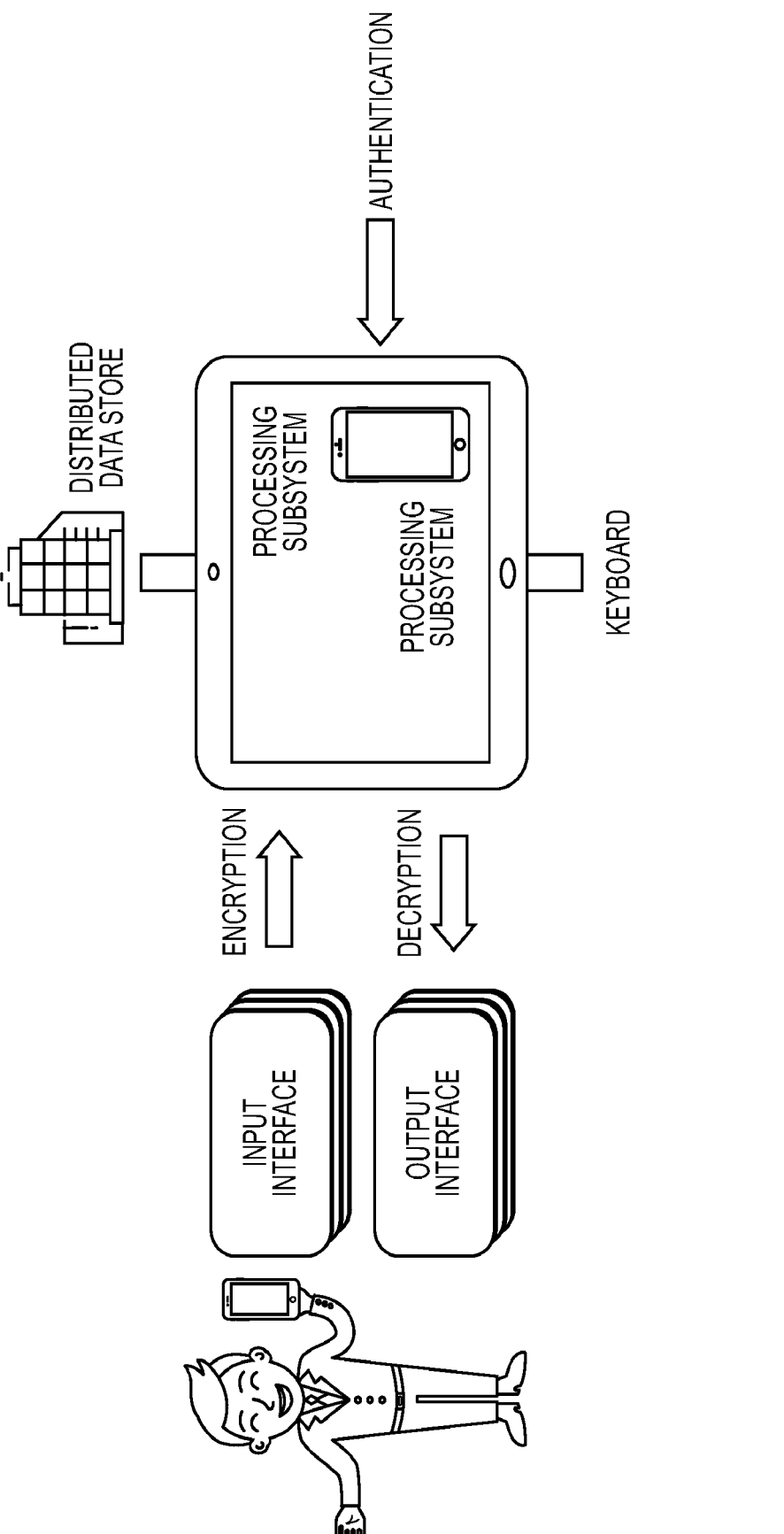
FIG. 12 illustrates certain embodiments of the methods and systems of the present technology in which the generated unique identifier can be used for authentication can be stored locally as well as remotely.
Figure 13:
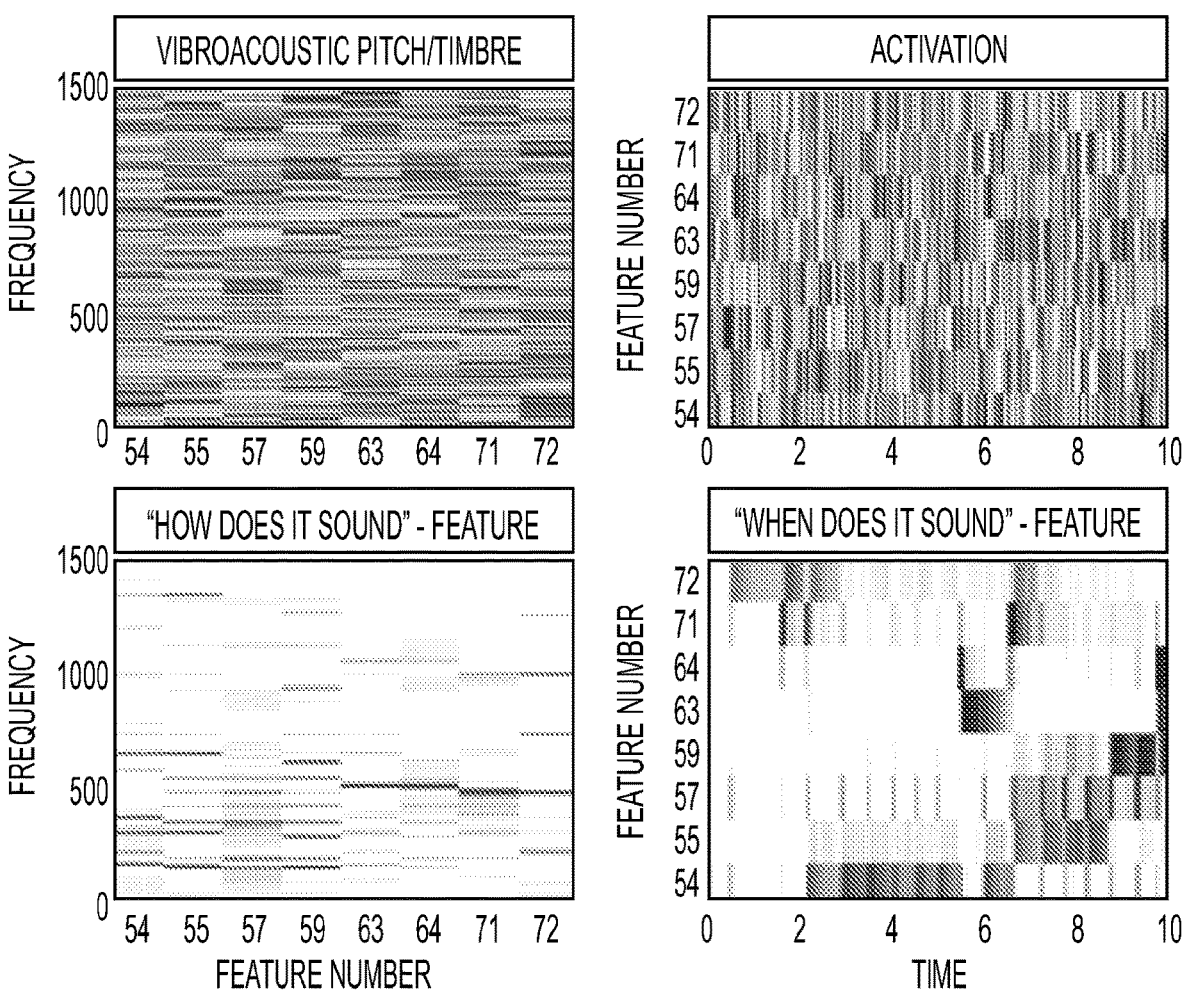
FIG. 13 illustrates extraction of identification markers from biometric data, according to certain embodiments of the present technology. The identification markers can be selected based on features which are more informative. The identification markers can be combined in any way.
Figure 14:
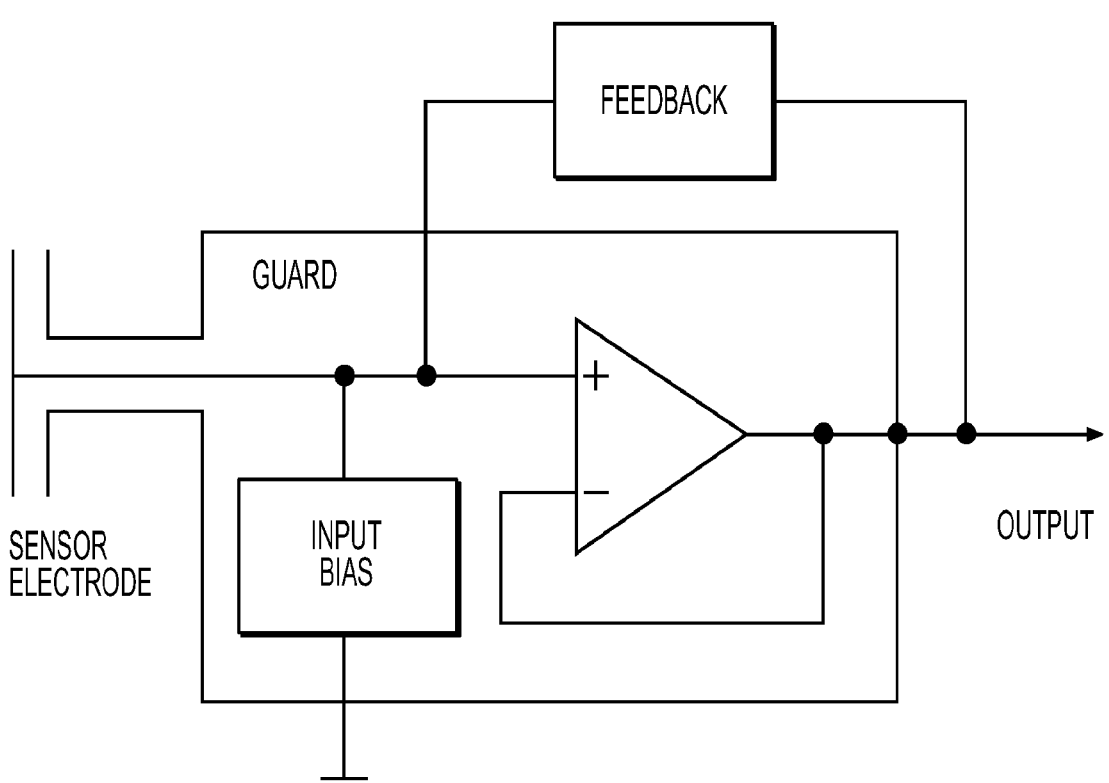
FIG. 14 is a block diagram of a non-limiting example of a bioelectric sensor described in U.S. Pat. No. 8,923,956B2, the contents of which are herein incorporated by reference.

FIG. 2 illustrates a computing environment 100, which may be used to implement and/or execute any of the systems and methods described herein. In some embodiments, the computing environment 100 may be implemented by any of a conventional personal computer, a network device and/or an electronic device (such as, but not limited to, a mobile device, a tablet device, a server, a controller unit, a control device, etc.), and/or any combination thereof appropriate to the relevant task at hand. In some embodiments, the computing environment 100 comprises various hardware components including one or more single or multi-core processors collectively represented by processor 110, a solid-state drive 120, a random access memory 130, and an input/output interface 150. The computing environment 100 may be a computer specifically designed to operate a machine learning algorithm (MLA). The computing environment 100 may be a generic computer system. The computer environment may comprise a stand alone device attachable to a mobile device for example.

In some embodiments, the computing environment 100 may also be a subsystem of one of the above-listed systems. In some other embodiments, the computing environment 100 may be an "off-the-shelf" generic computer system. In some embodiments, the computing environment 100 may also be distributed amongst multiple systems. The computing environment 100 may also be specifically dedicated to the implementation of the present technology. As a person in the art of the present technology may appreciate, multiple variations as to how the computing environment 100 is implemented may be envisioned without departing from the scope of the present technology.

Those skilled in the art will appreciate that processor 110 is generally representative of a processing capability. In some embodiments, in place of or in addition to one or more conventional Central Processing Units (CPUs), one or more specialized processing cores may be provided. For example, one or more Graphic Processing Units 111 (GPUs), Tensor Processing Units (TPUs), and/or other so-called accelerated processors (or processing accelerators) may be provided in addition to or in place of one or more CPUs. Further, in some embodiments, in place of or in addition to one or more conventional Central Processing Units (CPUs), one or more Field Programmable Gate Arrays (FGPAs) may be provided.

System memory will typically include random access memory 130, but is more generally intended to encompass any type of non-transitory system memory such as static random access memory (SRAM), dynamic random access memory (DRAM), synchronous DRAM (SDRAM), read-only memory (ROM), or a combination thereof. Solid-state drive 120 is shown as an example of a mass storage device, but more generally such mass storage may comprise any type of non-transitory storage device configured to store data, programs, and other information, and to make the data, programs, and other information accessible via a system bus 160. For example, mass storage may comprise one or more of a solid state drive, hard disk drive, a magnetic disk drive, and/or an optical disk drive.

Communication between the various components of the computing environment 100 may be enabled by a system bus 160 comprising one or more internal and/or external buses (e.g., a PCI bus, universal serial bus, IEEE 1394 "Firewire" bus, SCSI bus, Serial-ATA bus, ARINC bus, etc.), to which the various hardware components are electronically coupled.

The input/output interface 150 may allow enabling networking capabilities such as wired or wireless access. As an example, the input/output interface 150 may comprise a networking interface such as, but not limited to, a network port, a network socket, a network interface controller and the like. Multiple examples of how the networking interface may be implemented will become apparent to the person skilled in the art of the present technology. For example, the networking interface may implement specific physical layer and data link layer standards such as Ethernet, Fiber Channel, Wi-Fi, Token Ring or Serial communication protocols. The specific physical layer and the data link layer may provide a base for a full network protocol stack, allowing communication among small groups of computers on the same local area network (LAN) and large-scale network communications through routable protocols, such as Internet Protocol (IP).

The input/output interface 150 may be coupled to a touchscreen 190 or any other display device and/or to the one or more internal and/or external buses 160. The touchscreen 190 may equally be referred to as a screen 190. The touchscreen 190 may comprise touch hardware 194 (e.g., pressure-sensitive cells embedded in a layer of a display allowing detection of a physical interaction between a user and the display) and a touch input/output controller 192 allowing communication with the display interface 140 and/or the one or more internal and/or external buses 160. In some embodiments, the input/output interface 150 may be connected to a keyboard (not shown), a mouse (not shown) or a trackpad (not shown) allowing the user to interact with the computing device 100 in addition to or instead of the touchscreen 190.

According to some implementations of the present technology, the solid-state drive 120 stores program instructions suitable for being loaded into the random access memory 130 and executed by the processor 110 for executing acts of one or more methods 300 described herein. For example, at least some of the program instructions may be part of a library or an application.

In one embodiment, the system may comprise a device further comprising a sensor or plurality of sensors with its associated dedicated signal processing and computer system that can connect to another computing device such as mobile device such as a mobile phone, tablet computer, smart watch or laptop computer.

Data

In certain embodiments, methods and systems of the present technology are directed to collecting or monitoring biometric/biofield/biosignature data, which may be of high resolution or have a broad frequency bandwidth (such as 0.1 Hz to 160 kHz), and using cross-frequency coupling and cross-phase signal coupling methods, for example, to abstract biosignature data to a globally unique uDIDt-VeCx in the form of a QR code or other type of code. Once the biosignatures has been converted to an alphanumeric code or barcode it does not require any particular technology or cryptography to underpin the persistence, resolution or interpretation of uDIDt-VeCx.

TABLE 1

| Describes certain non-limiting examples of biometric data and data sources that may be utilized by the current technology | |
|---|---|
| Physiological | Hand/palm |
| | Fingerprint |
| | Face |
| | Iris |
| | DNA, oral/ear/nose under nail microbiome |
| | Vein patterns |
| | Multi-vibrome [head, throat, heart, lung, gut, bladder |

TABLE 1-continued

| Describes certain non-limiting examples of biometric data and data sources that may be utilized by the current technology | |
|---|---|
| | vibroacoustics] |
| | Multi-electrome [electrocardiogram (ECG), intracardiac electrogram (EGM), electromyography (EMG), electroencephalogram (EEG), electrooculography (EOG), galvanic skin response (GSR), etc] |
| | Skin, breath, and/or biofluid smell |
| Behavioral/ health related | Keystroke |
| | Handwriting |
| | Signature |
| | Voice print |
| | Speech pattern |
| | Vocalization (laugh, cough, etc) |

In certain embodiments, the collected or monitored data may comprise one or more of optical; electromagnetic and vibroacoustic monitored parameters.

The biometric data may be collected by any suitable device or system such as one or more sensors. The sensors may be any of those described herein and in International Patent Application No. PCT/US2021/046566, filed Aug. 18, 2021, each of which is incorporated by reference herein in its entirety.

In certain embodiments, biometric data is collected or monitored by one or more sensors, such as but not limited to: vibroacoustic sensor, electric potential sensor, volatile organic compound sensor and wide frequency bandwidth terahertz sensor (used to generate and detect electromagnetic waves at the terahertz frequencies), microphone, chemiresistive, optical, piezoelectric, electrochemical, surface acoustic wave (SAW), volatile organic compound sensor, altitude sensor, ambient temp sensor, barometric pressure sensor, and air quality sensor.

In certain embodiments, the biometric data may comprise a single data parameter which is collected and/or monitored. In certain other embodiments, the biometric data comprises two or more data parameters which are collected and/or monitored.

Data Collection

Biosensors are considered as devices that transform bio-physiological information into an analytically useful signal. For accurate and timely biometric evaluation, the biosensors need (i) accurate measurement, (ii) rapid assessment, and (iii) selective detection. In certain embodiments, biometric data is collected and/or monitored in one or both of a baseline phase and a base-line update phase along with environmental (contextual) determinants of physiological and pathophysiological health conditions to correct for signal drift).

In the baseline phase, biometric data may be collected and/or monitored over 1 to 5 days, 1 to 4 days, 1 to 3 days, 1 to 2 days, 2 to 5 days, 3 to 5 days, 4 to 5 days, 1 to 3 days, 2 to 3 days. Data collection may be continuous or in data segments.

In the update phase, biometric data may be collected and/or monitored for 1 to 25 seconds, 5 to 25 seconds, 10 to 25 seconds, 15 to 25 seconds, 20 to 25 seconds, 1 to 20 seconds, 1 to 15 seconds, 1 to 10 seconds, 5 to 10 seconds, 5 to 15 seconds.

In certain embodiments, methods and systems of creating the uDIDt-VeCx comprises acquiring data segments of about 15 s to about 20 s in length, or about 10 to about 25 s, or any other data segment length which satisfies data quality and data quantity requirements.

In certain embodiments, credentialing for health/travel passports during pandemic or disaster emergencies requires collection of data from about 2 days to about 4 days for continuous health characterization and baselining.

In certain embodiments, updates using baselined data requires a shorter confirmatory data read or top-up from about 5 seconds to about 10 seconds.

In certain embodiments, the method comprises acquiring biometric data of a subject at a first point in time, and storing in a database ("pre-screening step), The stored data may be used to generate the identifier at the first point in time, or at a second point in time which is later than the first point in time. The method further comprises, at the second point in time, using the stored data or the identifier as a "verifiable credential" or "keycard" for entry.

In certain embodiments, the method may further comprises obtaining digital image data of the subject's face or other body parts for ID purposes. This may occur at the first or second points in time.

The pre-screening process may be carried out over a period of about 1 to 5 days.

In certain embodiments, the generated unique identifier is used as a health passport. In certain embodiments, the baseline data is ephemeral (can be deleted, over written, or loses validity).

In certain embodiments, the generated unique identifier can be used for contact tracing. This can be helpful for maintaining privacy.

In certain embodiments, the method may comprise collecting and/or monitoring the data with sampling rates from about 0.01 Hz to about 1 GHz, more than about 1 GHz, about 10 GHz to about 100 GHz; about 0.01 Hz to about 10 THz. In certain embodiments, this can result in a more robust uDIDt-VeCx due to improved data quality and quality meaning. These sampling rates may be considered as "high resolution" compared to conventional data sampling. In the TeraHertz range, the date may be passively or actively captured.

In certain embodiments, the sensors used with embodiments of the present system and method may each capture data as catenated raw amplitude sequences or as combined short-time Fourier transform spectra.

In certain embodiments, the data from the sensors is captured from the subject in less than 15 seconds per subject, and preferably in less than 10 seconds per subject.

In certain embodiments, high resolution biometric/biofield/biosignature data is processed using cross-frequency coupling and cross-phase signal coupling methods to abstract biosignature data to a globally unique uDIDt-VeCx in the form of a QR code. In other embodiments, the unique identifier can be in any other format such as but not limited to: ultrasound beacons, infrared signals, radiofrequency (e.g. bluetooth) signal, electrical signals, alphanumeric, magnetic signal and not necessarily limited to optical signals.

In one embodiment, once the biosignatures has been converted to an alphanumeric code or barcode it does not require any particular technology or cryptography to underpin the persistence, resolution or interpretation of uDIDt-VeCx.

In certain embodiments, high resolution biometric/biofield/biosignature data is processed using inline cross-frequency coupling, harmonic progression, cross-phase signal coupling, super-learner, and/or structural machine learning methods to compute decomposable high dimensional matrices or a globally unique uDIDt-VeCx algebraic lattice. Those skilled in the art will appreciate that use of algebraic lattice(s) are the foundation of several of the leading quantum-resistant public-key cryptography in the National Institute of Standards and Technology (NIST) Post Quantum Cryptography (PQC) standards selection process.

Using the sensor fusion and data fusion of biometric signals within a Structural Machine Learning (SML) framework may provides a much higher degree of transparency and reproducibility than deep learning approaches, by expressing decision models as human-interpretable domain specific language (DSL) programs comprising steps of digital signal processing, mathematics of music, cardiopulmonary fluid dynamics, feature extraction, and ensembling. In particular, the DSL can be easily equipped (and then incrementally extended) with processing steps (functions) that capture concepts (processing steps, signal characteristics, etc.) that are proposed by biometrics experts. The SML framework may train effective biometric identification models from relatively smaller numbers of subjects compared to deep learning models and scales well with the amount of training data available, exhibiting monotonic increase of predictive power, while avoiding severe overfitting to the training set. The SML framework may handle multimodal identification and access control problems and decision classes and may be conveniently tuned with respect to the trade-off between sensitivity and specificity by inspecting the Receiver Operating Characteristic (ROC) curves, and can be used both in a 'soft' mode (scores/probabilities) as well as to produce 'crisp' binary identification decisions. The SML framework may be used to assess the 'informativeness' of biometric data inputs, e.g., the biometric identification "value" of individual biometric signal data streams, or combinations thereof. Synthesized features can be collected in 'libraries' and re-used in other usage scenarios, for instance to address other divergent identification, re-identification use cases. As a consequence of algorithm efficiency, the SML framework may produce models that are deployable on low-power hardware architectures, such as edge computer and/or edge inference in portable/field diagnostic equipment for wide deployment.

In some instances captured individuation biometric information available about individuals may be fragmentary and partial. In this sense, the nodes in the identification lattice can be considered to be analogous to individual pieces in a jigsaw puzzle: each biometric data stream has a number of specific inputs and outputs that only 'interlock' with compatible nodes. It is the task of the machine learning algorithm to impute missing data values in a consistent manner, which is analogous to synthesizing new compatible-jigsaw pieces. An example of this process, (in which the 'jigsaw pieces' are optimization algorithms of biometric data streams) is structural machine learning algorithms (encompassing digital signal processing, super-learner algorithms, cross-frequency coupling (CFC), adaptive filtering, harmonic progression, mathematical acoustics, and/or domain expertise) that extract mean vector length or modulation index, phase-locking value, envelope-to-signal correlation, analysis of amplitude spectra, analysis of coherence between amplitude and signal, analysis of coherence between the time course of power and signal, and eigen decomposition of multi-biometric data covariance matrices. These methods may also analyze how the frequency changes of a first signal influence the frequency of a second signal. The overall learning task is to complete a sufficiently large fragment of the overall biometric data jigsaw as to be able to yield a biosignature identifier with very low collision probability. The overall structural machine learning task is to complete a sufficiently large fragment of the overall biometric data jigsaw as to be able to yield a biosignature identifier with a very low collision probability.

In another embodiment, the verification process comprises the performance of the following steps:

Acquire live sample from candidate. This may be performed using sensors.

Extract prominent features from sample. This may be performed using one or more processing units.

Compare live sample with samples stored in database. This may be performed using algorithms.

Present the decision. The decision may be accepting or rejecting the candidate and/or authenticating or not authenticating the candidate.

In still another embodiment, the data processing subsystem comprises the performance of the following steps;

Sampling the data streams from the sensor or sensors

Sample signal acceptance/rejection

Sample signal enhancement

Sample signal normalization

Feature extraction

Cross frequency coupling and signal aggregation and abstraction

Comparison of the biometric sample with all stored samples in database.

In one embodiment, a distributed database store combines the enrolled sample and feature extraction and data abstraction and recall algorithms as interlaced data stores for additional security for the enrolled sample, i.e., data are algorithms and algorithms are data. Identification can be any memory from Random Access Memory (RAM), flash EPROM, or a data server.

In another embodiment, verification can be performed via smart phone or removable storage element like a contact or contactless smart card.

In some variations, verification can be performed via a ruggedized and tamper resistant uniquely verifiable hardware and verifiable FPGA circuits that proves its unforgeability.

In still another embodiment, the output interface communicates the decision of the biometric system to enable the access to the user. This can be a simple serial communication protocol RS232, or the higher bandwidth USB protocol. It could also be TCP/IP protocol, Radio Frequency Identification (RFID), Bluetooth, or an enhanced cellular protocol adequate to carry the biometric bandwidth.

In one embodiment disclosure defines the generic requirements for performing the four basic CRUD operations (create, read, update, deactivate) on the metadata associated with a uDIDt-VeCx (called the uDIDt-VeCx document): the generation of the aggregated biosignature underlying the original uDIDt-VeCx, the generic syntax underlying the original uDIDt-VeCx, and all subsequent uDIDts and VeCx, and verification and validation of uDIDt-VeCx variants.

The proposed generic approach is aimed to facilitate interoperability with any and all trusted infrastructures (e.g., blockchain, distributed ledger, decentralized file system, distributed database, peer-to-peer network). uDIDt-VeCx methods can also be developed for identifiers registered in federated or centralized identity management systems. This creates an interoperability bridge between the worlds of centralized, federated, and decentralized identifiers. Interoperability of implementations for uDIDt-VeCx and uDIDt-VeCx documents will be tested by evaluating an implementation's ability to create and parse DIDs and DID documents that conform to the specification. Interoperability for producers and consumers of uDIDt-VeCx and uDIDt-VeCx documents is provided by ensuring the DIDs and DID documents conform. Interoperability for DID method specifications is provided by the details in each DID method specification. It is understood that, in the same way that a web browser is not required to implement all known URI schemes, conformant software that works with uDIDt-VeCx is not required to implement all known uDIDt-VeCx methods (however, all implementations of a given uDIDt-VeCx method must be interoperable for that method).

Multiple base encoding formats are currently in preferred use by different blockchains, distributed ledgers, decentralized file systems, distributed databases, peer-to-peer networks. Commonly used base encoding formats used are Base58 (Bitcoin) [BASE58], base64url [RFC7515], base16 (hex) [RFC4648]. In one embodiment, a generic cipher intake approach supports interoperability. Thus, in one embodiment, the current technology provides for methods and systems that support the set of base encoding formats comprising Base58 (Bitcoin) [BASE58], base64url [RFC7515], and base16 (hex) [RFC4648].

Architecture Overview

Sensor Fusion

Natural processes of the human body yield a multitude of vibroacoustic signals, many of which are strongly attenuated at the skin—air interface. Motions with amplitudes and frequencies ranging from subtle vibrations to full-body kinematics contain diverse and important physiological health information that has not been fully characterized to date. Largely reproducible and regular heart, lung, and gastrointestinal contraction and relaxation cycle (individually and combined) mechanical vibrations generate complex fluctuating biofields that are further impacted by the thickness, elasticity/stiffness, hydration, injury/recovery, health/disease, etc., of cardiopulmonary cavities and tissues that far exceed the intuitive estimation of health/disease felt by physicians during palpation examination. When you speak, the air you exhale from your lungs is forced through closed vocal cords. This causes them to vibrate. They vibrate faster for higher-pitched sounds, and slower for lower-pitched sounds. With inspiration, the diaphragm and external intercostal muscles contract, decreasing pleural pressure that decreases alveolar pressures, thus drawing air into the lungs through the extrathoracic airway. With expiration, air flows out of the lungs. During quiet breathing, this process is largely passive deflation of the lungs due to lung recoil, but with active exhalation, expiratory muscles including abdominal and internal intercostal muscles also contribute. Airflow velocity, pressure, and wall shear stress changes occur for both inspiration (velocity splitting) and expiration (velocity merging). The level of changes in splitting and merging of airflow streamlines reflects the influence of respiratory mechanics of infection duration, intensity, and/or injury due to infection. During infection-related respiratory disorders, dramatic changes occur in the upper and lower respiratory tract.

Acoustic and digital stethoscopes acquire signals typically confined to a frequency range of 50 to 2,000 Hz, non-continuously and episodically. However, natural processes of the human body yield a multitude of mechanoacoustic signals, many of which strongly attenuate at the skin— air interface. Motions with amplitudes and frequencies ranging from subtle vibrations to full-body kinematics contain diverse and important physiological health information. Examples include vocal-fold vibrations, cardiac activity, respiration, pulse, airway fluid mechanics, gait and locomotion, respiration, and body orientation. A vibroacoustic biosignature system, such as a 0.01 Hz-160 kHz vibroacoustic biosignature system may extract information related to the mechanical impact of cavities, soft tissue, bone, and bodily fluids on cardiac, lung, and gastrointestinal contraction & relaxation signal shapes for diagnostic inference. Access to these novel data below current biological/medical instrumentation limits of detection provide a biometric signature that is immutable.

The current technology utilizes a novel active ultrahigh impedance capacitively coupled electric potential sensor (EPS), in certain embodiments. The absence of 1/f noise makes the EPS ideal for use with signal frequencies of −10 Hz or less. EPS can be used to measure both standard Electrocardiograph (ECG), galvanic skin response, electrooculography (EOG), electromyograph (EMG), and electroencephalography (EEG) by detecting the voltage change in muscles and nerves without electrical contact so there is no need to have electrodes on or in the body to detect current changes.

Sensors

Methods and systems of the current technology include one or more sensors, in certain embodiments. In certain embodiments, the system includes an array of sensors.

Generally, in some variations, embodiments of present methods and systems may utilize data from a sensing device including a vibroacoustic sensor module having one or more sensors configured to detect a vibroacoustic signal. Furthermore, in some variations, the vibroacoustic sensor module have a bandwidth ranging from about 0.01 Hz to at least about 160 kHz. Additionally, the sensing device may also include sensors other than for detecting vibroacoustic data.

Accordingly, in one aspect, the present technology pertains to a system for receiving and transducing biological events into electrical signals and determining a biosignature therefrom. In various embodiments, the sensor array comprises a vibro-acoustic sensor for measuring body sounds of the subject and a bio-electric sensor for measuring a bioelectric signal of the subject.

Developers have identified that subjects have biosignatures distinguishable from those of other subjects. The biosignatures may be derived directly from the collected data or from a processing of the collected data.

In some embodiments, the sensor array further comprises one or more sensors for measuring at least one environmental stimulus or condition. For example, the environmental stimulus or condition may be at least one of ambient temperature, barometric pressure, 9-axis motion, geolocation, location-dependent real-time weather conditions, ambient UV levels, pollen levels, or pollution.

In some embodiments, the sensor array comprises at least one sensor for measuring at least one of wavelength transmittance/absorbance; oxygen saturation; oxygen and/or carbon dioxide levels in exhaled breath; volatile organic compounds (VOC) in exhaled breath; skin temperature; differential body temperatures; body core temperature; body excretions; vocal tonal inflection; temporal artery movement; eye movement; eye pressure; chin movement; lip movement; shoulder movement; acoustic signals from any of the gut, gastrointestinal track, lower respiratory system, upper respiratory system; vascularization; skin color changes, and the like.

For measuring core temperature, for example, sensors may be used to detect temple artery motion and ocular tracking. The sensors may include one or more of an Acoustic Cardiograph (ACG), a ballistocardiograph (BCG), an electrocardiograph (ECG), an electromyograph (EMG), an electrooculograph (EOG), electroencephalograph (EEG), an ultrawide band sensor (UWB), which will be described in further detail below. The sensors can be passive sensors or active sensors.

In certain embodiments, at least one of the sensors is a contactless sensor. By contactless is meant that the sensor is physically spaced from the subject and does not require contact with the subject to collect data related to the subject. In certain embodiments, at least one other of the sensors does not require intimate contact with skin of the subject but requires contact with the subject through clothing or footwear. In certain embodiments, at least one of the sensors can sense electrical/electromagnetic signals associated with the subject. In certain embodiments, at least one other of the sensors can sense one or more of vibration signals, acoustic signals, heat signals, electromagnetic signals, magnetic signals associated with the subject, either in a passive or active manner.

Sensing Device

In some variations, the one or more sensors may be embodied in a sensing device including one or more of a vibroacoustic sensor module, a contextual sensor module, and/or an electronics system which may, for example, handle sensor data from the vibroacoustic sensor module and/or contextual sensor module. Some or all of these components may be enclosed or otherwise at least partially arranged in a housing, which may have any suitable form factor for different applications as further described below. In some variations, the housing may include a display for providing a user interface of the sensing device (e.g., for displaying information to a user, for permitting control of the sensing device, etc.).

The housing may include one or more openings and/or other structures to facilitate communication with sensors. For example, the housing may include a sensor opening adjacent to the vibroacoustic sensor module to permit entry and propagation of vibroacoustic waves toward the vibroacoustic sensor(s) in the module and/or a membrane or other receiver that interfaces with the vibroacoustic sensor(s). Additionally or alternatively, in some variations the sensing device may include an impedance matching diaphragm arranged in series with the vibroacoustic sensor module to improve sensitivity to a wide range of vibroacoustic frequencies. For example, impedance matching may refer to the operating state in which the load impedance and the internal impedance of the excitation source match to each other (e.g., within a tolerated impedance difference), thereby leading to a maximum power output. A mismatch in the impedances may result in undesirably high attenuation and/or reflection of source signals away from the vibroacoustic sensor module. This problem may be addressed, for example, by developing impedance matching circuits using machine-fabricated tunable components leveraging a plurality of diaphragm cutout designs for an optimal dynamic range in the low infrasound domain. A combined dome/transducer solution may include a suitable protective material (e.g., rubber, felt liner, light foam, etc.) around the diaphragm and fixture area to protect the interior of the transducer from water and particulate matter. Diaphragm may include a passive material (including but not limited to polymer, polyamide, polycarbonate, polypropylene, carbon fiber, fiber glass, etc.) fabricated as the structural layer with optimized dimensions for the physical system form factor. In order to obtain the tunable impedance matching system and structural layer(s), the gap between the diaphragm and embedded electrodes may be tunable. The structural layer(s) may be spun and patterned to ensure the shape and optimal weight and subsequently bonded.

In some variations, the sensing device may include one or more sensors (e.g., proximity sensors, Hall effect sensors, contact sensors, etc.) that detect and authenticate the attachment and detachment of replaceable parts, so that the sensing device can intelligently monitor uses, sterile change events, duration of use between changes in sterile covers, battery levels, number of uses and/or other usage data, etc. Such data may, for example, be used to monitor a report on compliance with best practices and required protocols for maintaining cleanliness.

Vibrometer Sensor Module

The vibroacoustic sensor module may include one or more sensors for detecting a wide spectrum of vibroacoustic frequencies, which may provide useful in determining suitable identifiers for a subject. The threshold of human audibility decreases sharply as vibrational frequency falls below about 500 Hz. However, in a healthy individual at rest, most cardiac, respiratory, digestive, and movement-related information is inaudible to humans, as this information occurs at frequencies below those associated with speech. By using a broad spectrum of infrasound, ultrasound, and far-ultrasound vibroacoustic frequencies in embodiments of the present technology, a pool of data from which to determine an identifier for the subject is increased.

Example sensing devices and vibroacoustic sensor modules are described below. Such devices and methods are primarily described with respect to characterizing a bodily condition of a subject, which may be, for example, a human or other animal (e.g., for human healthcare and/or veterinary care). However, it should be understood that other applications of the sensing devices and methods may relate to characterization of non-living items, including but not limited to heating, ventilation, air conditioning (HVAC) systems, car engines, bridges, aircraft wings, environmental infrasound, ballistics, drone and/or seacraft identification etc. For example, the sensing devices and methods may be applied to characterize structural health (e.g., characterizing structural integrity of bridges, buildings, aircraft, vehicles, etc.), environmental noise pollution, rotating motor engine performance optimization, surveillance etc.

A vibroacoustic sensor module may include one or more sensors (e.g., MEMS sensors) configured to detect a vibroacoustic signal, and one or more deflecting structures interfacing with one or more of the sensors. For example, the one or more sensors may be selected and/or arranged to interface with the one or more deflecting structures so as to measure various characteristics of the movement of the deflecting structure(s) (e.g., in response to vibroacoustic waves). Such movement, which is measurable by the one or more sensors, may be analyzed to assess bodily condition(s) of a subject. As further described below, in some variations, the one or more sensors may also be arranged on a flexible circuit board or other structure that is suitably flexible so as to not significantly interfere with the interfacing of the sensor(s) and deflecting structure(s), thereby avoiding reduction in sensitivity and/or bandwidth of the vibroacoustic sensor module. Exemplary variations of sensor arrangements and deflecting structures are described in further detail below.

In some variations, the vibroacoustic sensor module may have a bandwidth suitable for detecting vibroacoustic signals in the infrasound range, such as a bandwidth ranging from about 0.01 Hz to at least about 20 Hz. Furthermore, in some variations, the vibroacoustic sensor module may have wider bandwidths covering a wider spectrum of infrasound-to-ultrasound, such as a bandwidth ranging from about 0.01 Hz to at least 160 kHz. The vibroacoustic sensor module may, in some variations, include a suite of multiple vibroacoustic sensors, each having a respective bandwidth forming a segment of the overall vibroacoustic sensor module bandwidth. At least some of these multiple vibroacoustic sensors may have respective bandwidths that at least partially overlap. Accordingly, various sensor module bandwidths may be achieved based on a selection of particular vibroacoustic sensors that collectively contribute to a particular sensor module bandwidth. In other words, bandwidth extension and linearization approach (bandwidth predistortion) may utilize modular sensor fusion and response feedback information, such as to compensate for bandwidth limitations of any particular single sensor with overlapped combinations of sensors to cover a wider bandwidth with optimal performance. For example, in some variations the vibroacoustic sensor module may have an overall bandwidth ranging from about 0.01 Hz to at least about 50 kHz, from about 0.01 Hz to at least about 60 kHz, from about 0.01 Hz to at least about 70 kHz, from about 0.01 Hz to at least about 80 kHz, from about 0.01 Hz to at least about 90 kHz, from about 0.01 Hz to at least about 100 kHz, from about 0.01 Hz to at least about 110 kHz, from about 0.01 Hz to at least about 120 kHz, from about 0.01 Hz to at least about 130 kHz, from about 0.01 Hz to at least about 140 kHz, from about 0.01 Hz to at least about 150 kHz, from about 0.01 Hz to at least about 160 kHz or more.

For example, the vibroacoustic sensor module may include one or more sensors (e.g., MEMS sensors) including a microphone, accelerometer, pressure sensors, piezoelectric transducer elements, etc. For example, the vibroacoustic sensor module may include one or more microphones such as a dynamic microphone, a large diaphragm condenser microphone, a small diaphragm condenser microphone, and/or a ribbon microphone. Additionally, or alternatively, the vibroacoustic sensor module may include a linear position transducer. Such sensors may be configured to detect and measure vibroacoustic signals by interfacing with a suitable deflecting structure that moves in response to a vibroacoustic signal. In some variations, the vibroacoustic sensor module may combine multiple microelectromechanical systems technologies cross-axis inertial sensors capable of detecting vibroacoustic signals ranging from about 20 Hz to about 20 kHz. Additionally, or alternatively, the vibroacoustic sensor module may include a MEMS cross-axis inertial sensor fusion capable of detecting vibroacoustic signals ranging from about 1 Hz (or less) to a few kHz (e.g., between about 1 Hz and about 2 kHz). Even further, the vibroacoustic sensor module may additionally or alternatively include a MEMS cross-axis inertial sensor capable of detecting vibroacoustic signals ranging from about 0.01 Hz to several hundred Hz (e.g., between about 0.005 Hz and about 1 kHz, or about 0.05 and about 1 kHz). Additionally, or alternatively, other suitable vibroacoustic sensors may be included in the vibroacoustic sensor module, such as a voice coil transducer, piezoelectric transducer, etc. In some variations, transmission of vibroacoustic waves may occur through an intermediate medium such as air and/or across a deflecting structure.

Furthermore, a suite of multiple kinds of sensors in the vibroacoustic sensor module may be configured to more fully capture longitudinal and transverse vibrations, as well as environmental context and environmental disturbances (alone or in combination with the contextual sensor module described in further detail below). In some variations, environmental context signals may be useful for contextualizing the relevant vital physiology data collected. Additionally, or alternatively, in some variations, environmental disturbance data (e.g., ambient noise) may be used for noise cancellation from the relevant biological vibroacoustic signal component. Such noise cancellation may, for example, be performed as active noise cancellation on the device, or as a postprocessing step.

Deflecting Structures

In some variations, the vibroacoustic sensor module has a deflecting structure having a nominal or resting configuration in which the deflecting structure is arranged in a plane, and the deflecting structure may deflect or flex in response to out-of-plane forces. In these variations, the deflecting structure may be configured to have low stiffness (or resistance) against out-of-plane movement with good compliance to skin movement, yet high stiffness or resistance against in-plane movement and low crosstalk between axes within the plane. Accordingly, a deflecting structure have high sensitivity to acoustic waves directed toward the deflecting structure (that is, acoustic waves having a vector component that is orthogonal to the deflecting structure) but be robust against noise contributed by other forces.

Furthermore, in some variations, a deflecting structure in the vibroacoustic sensor module may have relatively low mass on the movable portion of the deflecting structure to reduce inertia (and further improve sensitivity to out-of-plane forces). In some variations, the deflecting structure may be designed with low or no hysteresis, such that out-of-plane movement is highly linear. Additionally, or alternatively, the deflecting structure may be designed to have low material fatigue over time, so as to be predictable and consistent over the long-term use of the sensing device.

The deflecting structure may, in some variations, include a more rigid material such as a rigid plastic, and may be formed through 3D printing, milling, injection molding, or in any suitable manner. For example, the deflecting structure may include a material including but not limited to polyamide, polycarbonate, polypropylene, carbon fiber, fiber glass, and/or other suitable material.

Membrane-Type Sensor Modules

In some variations, the deflecting structure may include a membrane, and one or more sensors may be arranged to interface with the membrane to detect the membrane's out-of-plane movement in response to vibroacoustic signals. For example, a vibroacoustic sensor module may include a deflecting structure having a membrane extending across a frame, and an accelerometer coupled to a central region of the membrane via a flexible circuit board. The membrane may include a thin sheet or diaphragm of flexible material that is taut over the frame, such as an elastomeric material (e.g., latex, nitrile, etc.). In some variations, the membrane may be coupled to the frame with one or more suitable fasteners, such as a clamp ring that radially compresses and secures the membrane to the frame, other suitable fasteners (e.g., epoxy) or in any other suitable manner. In some variations, FEM design optimization models suggest an optimal dome thickness range of 10 to 5000 micrometers and diameter between about 2 5 millimeters and about 75 millimeters. One goal of the dome is to enable collection of high data fidelity while providing a comfortable, non-irritating data harvest interface. The dome material may be configured to deform naturally with low amplitude movements of the body. For example, in some variations, the dome design may incorporate deformable, non-coplanar interconnects, a strain-isolation layer at the base, a soft-encapsulation overlayer and/or a hollow air-pocket configuration. Together, these features may provide low-modulus, elastic mechanics for ultrasensitive signal pickup.

Similar to the flexure arm-based variations of vibroacoustic sensor modules described above, the vibroacoustic sensor module may include a flexible circuit board that is flexible and receptive to out-of-plane forces. For example, a flexible circuit board that has a zig-zag shape, but it should be understood that the flexible circuit may alternatively have a spiral or any suitable shape. The flexible circuit board may have an inner end having an accelerometer and an outer end having a cable connector, with conductive traces extending between the accelerometer and the cable connector for signal communication to and from the accelerometer. In some variations, at least the inner end the flexible circuit board may be coupled to the membrane with epoxy or any other suitable fastener or in any suitable manner. Accordingly, movement of the membrane may be tracked and measured by the accelerometer, and corresponding vibroacoustic sensor signals from the accelerometer may be analyzed such as for detecting one or more bodily conditions of a subject.

Additionally or alternatively, in some variations, a vibroacoustic sensor module may include a membrane-based deflecting structure that interfaces with or interacts with one or more sensors across a cavity. For example, a vibroacoustic sensor module may include a deflecting structure having a cavity that is sealed by a membrane extending across a frame. In some variations, the deflecting structure may include a handle portion may be handheld (and/or be used to secure to another portion of the sensing device).

The membrane may be constructed and attached in a manner similar to that described above. Furthermore a rigid circuit board can include one or more sensors and cable connectors. Signals to and from the sensor(s) may be communicated via conductive traces extending between the sensor(s) and a cable connector. The rigid circuit board may be positioned in the vibroacoustic sensor module such that the one or more sensors are located within or adjacent the cavity (or otherwise arranged in fluid communication with the cavity, such as through an opening), a sensor may be located opposite the membrane. In such arrangements, deflection of the membrane in response to vibroacoustic waves may cause changes within the cavity that are detectable and measurable by the one or more cross-axis inertial sensors. For example, in some variations the one or more sensors may include a pressure sensor (e.g., MEMS pressure sensor) that detects pressure variations in the cavity induced by the deflection of the membrane. For example, the pressure sensor may be read at a high rate (e.g., more than about 500 Hz) and the pressure data may be used to construct a low frequency signal waveform (e.g., between about 0.01 Hz to about 1 kHz). As another example, in some variations the one or more sensors may include a microphone (e.g., MEMS microphone) that detects vibroacoustic waves traversing the cavity and induced by deflection of the membrane. The microphone may be configured to sense a different bandwidth, such as between about 5 Hz to about 4 kHz. Furthermore, in some variations, the one or more sensors may include both a pressure sensor and a microphone, and/or any other suitable sensors (e.g., voice coil transducer, piezoelectric transducer, etc.).

In some variations, a vibroacoustic sensor module may include a dampening feature to help isolate the sensing components from hand movements that may introduce noise and/or error into the acquired vibroacoustic signals. For example, a variation of a vibroacoustic sensor module that is similar to that described above, in that the vibroacoustic sensor module may include a deflecting structure having a cavity that is sealed by a membrane extending across a frame. The deflecting structure may include an annular handle portion that is indirectly coupled to the central frame via a flexible layer and/or other suitable flexible structures that help isolate the sensing components (e.g., sensor(s), membrane, etc.) from hand pressure and other movement variations. The flexible layer may, for example, include a dampening material such as foam or an elastomeric material, and/or include dampening structures such as radial ribs that help dampen and/or decouple movements from the handle from the rest of the deflecting structure. The dampening could also be implemented in other "active" ways with one or more controlled mechanisms or materials, such as actuators (e.g., micro- and or servo motors), piezoelectric or electrosensitive polymers, etc.

Other Vibroacoustic Sensor Modules

The sensor or sensing device from which data can be used for the present technology is not particularly limited. For example, data of the subject can be that obtained by any one or more systems as described in U.S. 63/075,059, filed Sep. 4, 2020, U.S. 63/075,056, filed Sep. 4, 2020, U.S. Ser. No. 17/096,806, filed Nov. 12, 2020, International Patent Application No. PCT/IB32021/053919, filed May 8, 2021, International Patent Application No. PCT/US2021/046566, filed Aug. 18, 2021, and a concurrently filed PCT application entitled "NON-CONTACT SENSOR SYSTEMS AND METHODS", which are all incorporated by reference herein in their entirety.

Electrical/Electromagnetic Sensing (Bio-Electric Sensing)

The dipole is the elemental unit of cardiac activity. Each dipole consists of a positive (+) and negative (−) charge generated by the action of ion channels. As activation spreads, the sources sum together and act as a continuous layer of sources. Stated simply, an electric dipole consists of two particles with charges equal in magnitude and opposite in sign separated by a short distance. In the heart, the charged particles are ions such as sodium ($Na^-$), potassium ($K^+$), calcium ($Ca_2^+$), phosphates ($PO_43^-$), and proteins. The separation is the distance across the cardiac cell membrane. Because they are too large to pass through the small cell membrane channels, the negatively charged particles remain in the cell, whereas the positive ions move back and forth through specific channels and "ion pumps" to create polarization and depolarization across the membrane.

If enough dipoles are present together, they create a measurable voltage. Resting cardiac cells within the heart are normally at −70 mV. This means that at rest, there is naturally a charge imbalance present in the heart. This imbalance, called polarization of the cell, attracts positive ions toward the interior of the cell. When a cardiac cell is activated by an outside stimulus, channels in the cell membrane activate, and the excess positive ions outside of the cell rush into the cell. This process, called depolarization, makes the cell less negatively charged and is associated with "activation" of the cardiac cell. When millions of these cells activate together, the heart contracts and pumps blood to the rest of the body. The combined activation of these cells generates enough voltage to be measured on the surface of the skin by an electrocardiogram (ECG). The resulting intracardiac electrogram (EGM) extends beyond the area of the dipole signal by a factor of five, reducing resolution and acuity.

Embodiments of the present technology utilize the signal produced by physiological and, in some embodiments, environmental sensors to infer, computationally, a physiological parameter of the patient. The physiological sensors, may include a vibro-acoustic sensor in contact with a patient over at least the frequency band 0.001 Hz to 160 kHz and a bio-electric sensor to measure electrical fields and electrical impulses, and optionally various other sensors described in detail herein.

The physiological parameter may be the magnitude or existence of an internal process, such as blood flow; the presence of a biomarker; or the existence or likelihood of a disease. In some embodiments, the computational inference is based on additional data such as the patient's position, orientation, environmental, and/or historical health information of the patient. Biosensors in accordance herewith separate dipole density from voltage to increase diagnostic specificity and capability.

ACG—Acoustocardiography

The ACG records the vibrations of the heart as the blood moves through the various chambers, valves, and large vessels, hence the name Acoustic CardioGraph. The ACG records these vibrations at four locations of the heart and provides a "graph signature." While the opening and closing of the heart valves contributes to the graph, so does the contraction and strength of the heart muscle. As a result, a dynamic picture is presented of the heart in motion. If the heart is efficient and without stress, the graph is smooth and clear. If the heart is inefficient, there are definite patterns associated each type of contributing dysfunction. The ACG is not the same as an EKG, which is a common diagnostic test. The electrocardiograph (EKG or ECG) records the electrical impulses as it moves through the nerves of the heart tissue as they appear on the skin. The EKG primarily indicates if the nervous tissue network of the heart is affected by any trauma, damage (for example from a prior heart attack or infection), severe nutritional imbalances, stress from excessive pressure. Only the effect on the nervous system is detected. It will not tell how well the muscle or valves are functioning, etc. In addition, the EKG is primarily used to diagnose a disease. The ACG not only looks at electrical function but also looks at heart muscle function, which serves as a window of the metabolism of the entire nervous system and the muscles. Using the heart allows a "real-time" look at the nerves and muscles working together. As a result of this interface, unique and objective insights into health of the heart and the entire person can better be seen.

ACG—Passive Acoustocerebrography

All brain tissue is influenced by blood circulating in the brain's vascular system. With each heartbeat, blood circulates in the skull, following a recurring pattern according to the oscillation produced. This oscillation's effect, in turn, depends on the brain's size, form, structure and its vascular system. Thus, every heartbeat stimulates minuscule motion in the brain tissue as well as cerebrospinal fluid and therefore produces minimal changes in intracranial pressure. These changes can be monitored and measured in the skull. Passive sensors like accelerometers can be used to identify these signals correctly. Sometimes highly sensitive microphones can be used.

ACG—Active Acoustocerebrography

In active ACG applications, a multi-frequency ultrasonic signal is used to detect and classify adverse changes at the cellular or molecular level. In addition to all of the advantages that passive ACG provides, with active ACG it is possible to conduct a spectral analysis of the acoustic signals received. These spectrum analyses not only display changes in the brain's vascular system, but also those in its cellular and molecular structures. One common application of active ACG is the Transcranial Doppler test. More recently, its color version (TCCD) has been deployed. These ultrasonic procedures measure blood flow velocity within the brain's blood vessels. They can diagnose embolisms, stenoses and vascular constrictions, for example, in the aftermath of a subarachnoid hemorrhage.

BCG—Ballistocardiography

The ballistocardiograph (BCG) is a measure of ballistic forces generated by the heart. The downward movement of blood through the descending aorta produces an upward recoil, moving the body upward with each heartbeat. As different parts of the aorta expand and contract, the body continues to move downward and upward in a repeating pattern. Ballistocardiography is a technique for producing a graphical representation of repetitive motions of the human body arising from the sudden ejection of blood into the great vessels with each heartbeat. It is a vital sign in the 1-20 Hz frequency range which is caused by the mechanical movement of the heart and can be recorded by noninvasive methods from the surface of the body. Main heart malfunctions can be identified by observing and analyzing the BCG signal. BCG can also be monitored using a camera based system in a non-contact manner. One example of the use of a BCG is a ballistocardiographic scale, which measures the recoil of the person's body who is on the scale. A BCG scale is able to show a person's heart rate as well as their weight.

EKG (ECG)

The electrocardiograph (EKG or ECG) records the electrical impulses as it moves through the nerves of the heart tissue as they appear on the skin. The EKG primarily indicates if the nervous tissue network of the heart is affected by any trauma, damage (for example from a prior heart attack or infection), severe nutritional imbalances, stress from excessive physiological or psychological stress.

EMG

Electromyography (EMG) is an electrodiagnostic medicine technique for evaluating and recording the electrical activity produced by skeletal muscles. EMG is performed using an instrument called an electromyograph to produce a record called an electromyogram. An electromyograph detects the electric potential generated by muscle cells when these cells are electrically or neurologically activated. The signals can be analyzed to detect medical abnormalities, activation level, or recruitment order, or to analyze the biomechanics of human or animal movement. EMG can also be used in gesture recognition.

EOG

Electrooculography (EOG) is a technique for measuring the corneo-retinal standing potential that exists between the front and the back of the human eye. The resulting signal is called the electrooculogram. Primary applications are in ophthalmological diagnosis and in recording eye movements. Unlike the electroretinogram, the EOG does not measure response to individual visual stimuli.

To measure eye movement, pairs of electrodes are typically placed either above and below the eye or to the left and right of the eye. If the eye moves from center position toward one of the two electrodes, this electrode "sees" the positive side of the retina and the opposite electrode "sees" the negative side of the retina. Consequently, a potential difference occurs between the electrodes. Assuming that the resting potential is constant, the recorded potential is a measure of the eye's position.

EOG

Electro-olfactography or electroolfactography (EOG) is a type of electrography (electrophysiologic test) that aids the study of olfaction (the sense of smell). It measures and records the changing electrical potentials of the olfactory epithelium, in a way similar to how other forms of electrography (such as ECG, EEG, and EMG) measure and record other bioelectric activity.

Electro-olfactography is closely related to electroantennography, the electrography of insect antennae olfaction.

EEG

Electroencephalography (EEG) is an electrophysiological monitoring method to record electrical activity of the brain. It is typically noninvasive, with the electrodes placed along the scalp, although invasive electrodes are sometimes used, as in electrocorticography. EEG measures voltage fluctuations resulting from ionic current within the neurons of the brain. Clinically, EEG refers to the recording of the brain's spontaneous electrical activity over a period of time, as recorded from multiple electrodes placed on the scalp. Diagnostic applications generally focus either on event-related potentials or on the spectral content of EEG. The former investigates potential fluctuations time locked to an event, such as 'stimulus onset' or 'button press'. The latter analyses the type of neural oscillations (popularly called "brain waves") that can be observed in EEG signals in the frequency domain.

EEG can be used to diagnose epilepsy, which causes abnormalities in EEG readings. It can also used to diagnose sleep disorders, depth of anesthesia, coma, encephalopathies, and brain death. EEG, as well as magnetic resonance imaging (MRI) and computed tomography (CT) can be used to diagnose tumors, stroke and other focal brain disorders. Advantageously, EEG is a mobile technique available and offers millisecond-range temporal resolution which is not possible with CT, PET or MRI.

Derivatives of the EEG technique include evoked potentials (EP), which involves averaging the EEG activity time-locked to the presentation of a stimulus of some sort (visual, somatosensory, or auditory). Event-related potentials (ERPs) refer to averaged EEG responses that are time-locked to more complex processing of stimuli.

UWB

Ultra-wideband (also known as UWB, ultra-wide band and ultraband) is a radio technology that can use a very low energy level for short-range, high-bandwidth communications over a large portion of the radio spectrum. UWB has traditional applications in non-cooperative radar imaging. Most recent applications target sensor data collection, precision locating and tracking applications.

A significant difference between conventional radio transmissions and UWB is that conventional systems transmit information by varying the power level, frequency, and/or phase of a sinusoidal wave. UWB transmissions transmit information by generating radio energy at specific time intervals and occupying a large bandwidth, thus enabling pulse-position or time modulation. The information can also be modulated on UWB signals (pulses) by encoding the polarity of the pulse, its amplitude and/or by using orthogonal pulses. UWB pulses can be sent sporadically at relatively low pulse rates to support time or position modulation, but can also be sent at rates up to the inverse of the UWB pulse bandwidth. Pulse-UWB systems have been demonstrated at channel pulse rates in excess of 1.3 gigapulses per second using a continuous stream of UWB pulses (Continuous Pulse UWB or C-UWB), supporting forward error correction encoded data rates in excess of 675 Mbit/s.

A valuable aspect of UWB technology is the ability for a UWB radio system to determine the "time of flight" of the transmission at various frequencies. This helps overcome multipath propagation, as at least some of the frequencies have a line-of-sight trajectory. With a cooperative symmetric two-way metering technique, distances can be measured to high resolution and accuracy by compensating for local clock drift and stochastic inaccuracy.

Another feature of pulse-based UWB is that the pulses are very short (less than 60 cm for a 500 MHz-wide pulse, and less than 23 cm for a 1.3 GHz-bandwidth pulse)—so most signal reflections do not overlap the original pulse, and there is no multipath fading of narrowband signals. However, there is still multipath propagation and inter-pulse interference to fast-pulse systems, which must be mitigated by coding techniques.

Ultra-wideband is also used in "see-through-the-wall" precision radar-imaging technology, precision locating and tracking (using distance measurements between radios), and precision time-of-arrival-based localization approaches. It is efficient, with a spatial capacity of approximately 1013 bit/s/m². UWB radar has been proposed as the active sensor component in an Automatic Target Recognition application, designed to detect humans or objects that have fallen onto subway tracks.

Ultra-wideband pulse Doppler radars can also be used to monitor vital signs of the human body, such as heart rate and respiration signals as well as human gait analysis and fall detection. Advantageously, UWB has less power consumption and a high-resolution range profile compared to continuous-wave radar systems. However, its low signal-to-noise ratio has made it vulnerable to errors.

In the USA, ultra-wideband refers to radio technology with a bandwidth exceeding the lesser of 500 MHz or 20% of the arithmetic center frequency, according to the U.S. Federal Communications Commission (FCC). A Feb. 14, 2002 FCC Report and Order authorized the unlicensed use of UWB in the frequency range from 3.1 to 10.6 GHz. The FCC power spectral density emission limit for UWB transmitters is −41.3 dBm/MHz. This limit also applies to unintentional emitters in the UWB band (the "Part 15" limit). However, the emission limit for UWB emitters may be significantly lower (as low as −75 dBm/MHz) in other segments of the spectrum.

Deliberations in the International Telecommunication Union Radiocommunication Sector (ITU-R) resulted in a Report and Recommendation on UWB in November 2005. UK regulator Ofcom announced a similar decision on 9 Aug. 2007. More than four dozen devices have been certified under the FCC UWB rules, the vast majority of which are radar, imaging or locating systems.

There has been concern over interference between narrowband and UWB signals that share the same spectrum. Earlier, the only radio technology that used pulses were spark-gap transmitters, which international treaties banned because they interfere with medium-wave receivers. UWB, however, uses lower power. The subject was extensively covered in the proceedings that led to the adoption of the FCC rules in the U.S. and in the meetings relating to UWB of the ITU-R leading to its Report and Recommendations on UWB technology. Commonly used electrical appliances emit impulsive noise (for example, hair dryers) and proponents successfully argued that the noise floor would not be raised excessively by wider deployment of low power wideband transmitters.

SCG

Seismocardiography (SCG) is the non-invasive measurement of cardiac vibrations transmitted to the chest wall by the heart during its movement. SCG was first introduced around the mid 20th century. Some promising clinical applications were suggested. These include the observation of changes in the SCG signal due to ischemia and the use of SCG in cardiac stress monitoring. The origin of SCG can be traced back to the 19th century when scientists reported observing a heartbeat while standing on a scale.

Although SCG in general has not been deployed in the clinical environment, some promising applications have been suggested. For instance, SCG has been proposed to be of value in assessing the timing of different events in the cardiac cycle. Using these events, assessing, for example, myocardial contractility might be possible. SCG has also been proposed to be capable of providing enough information to compute heart rate variability estimates. A more complex application of cardiac cycle timings and SCG waveform amplitudes is the computing of respiratory information from the SCG.

VOC Excretion

Exhaled breath in a subject may include volatile organic compounds or semi-volatile organic compounds. The potential of exhaled breath analysis is huge, with applications in many fields including, but not limited to, the diagnosis and monitoring of disease.

Certain VOCs are linked to biological processes in the human body. For instance, dimethylsulfide is exhaled as a result of fetor hepaticus and acetone is excreted via the lungs during ketoacidosis in diabetes.

Typically, VOC Excretion or Semi-Volatile Organic Compound Excretion can be measured using plasmon surface resonance, mass spectroscopy, enzymatic based, semiconductor based or imprinted polymer based detectors.

VTI

Vocal tone inflection analysis can be indicative of an array of mental and physical conditions that make you slur your words, elongate sounds, or speak in a more nasal tone. They may even make your voice creak or jitter so briefly that it's not detectable to the human ear. Furthermore, vocal tone changes can also be indicative of upper or lower respiratory conditions, as well as cardiovascular conditions.

Capacitive Sensors

Capacitive/Non-contact electrodes were developed since the absence of impedance adaptation substances could make the skin-electrode contact instable over time. This difficulty was addressed by avoiding physical contact with the scalp through non-conductive materials (i.e., a small dielectric between the skin and the electrode itself): despite the extraordinary increase of electrode impedance (>200 MOhm), in this way it will be quantifiable and stable over time.

A particular type of dry electrode, is known as a capacitive or insulated electrode. These electrodes require no ohmic contact with the body since it acts as a simple capacitor placed in series with the skin, so that the signal is capacitively coupled. The received signal can be connected to an operational amplifier and then to standard instrumentation.

The use of a dielectric material in good contact to the skin results in a fairly large coupling capacitance, ranging from 300 pF to several nano-farads. As a result, a system with reduced noise and appropriate frequency response is readily achievable using standard high-impedance FET (field-effect transistor) amplifiers.

While wet and dry electrodes require physical contact with the skin to function, capacitive electrodes can be used without contact, through an insulating layer such as hair, clothing or air. These contactless electrodes have been described generally as simple capacitive electrodes, but in reality there is also a small resistive element, since the insulation also has a non-negligible resistance.

Capacitive sensors can be used to measure heart rate in humans via either direct skin contact or through one and two layers of clothing with no dielectric gel and no grounding electrode, and to monitor respiratory rate. High impedance electric potential sensors can also be used to measure breathing and heart signals.

Vibro-Acoustic Sensors

Stethoscopes are widely used by health professionals to aid in the detection of body sounds. The procedures for listening to and analyzing body sounds, called auscultation, are often difficult to learn due to the typically low sound volume produced by an acoustic stethoscope. Electronic stethoscopes have been developed to amplify the faint sounds from the body. However, such devices may suffer from distortion and ambient noise pickup. The distortion and noise are largely due to the performance of the acoustic-to-electrical transducers, which differ in operation from the mechanical diaphragms used in acoustic stethoscopes.

Traditional acoustic stethoscopes convert the movement of the stethoscope diaphragm into air pressure, which is directly transferred via tubing to the listener's ears. The listener therefore hears the direct vibration of the diaphragm via air tubes. Unfortunately, inefficient acoustic energy transfer via the air tubes causes diminished volume and sound clarity. Existing electrical stethoscope transducers are typically one of two types: (1) microphones mounted behind the stethoscope diaphragm, or (2) piezo-electric sensors mounted on, or physically connected to, the diaphragm.

Microphones mounted behind the stethoscope diaphragm pick up the sound pressure created by the stethoscope diaphragm, and convert it to electrical signals. The microphone itself has a diaphragm, and thus the acoustic transmission path comprises or consists of a stethoscope diaphragm, the air inside the stethoscope housing, and finally the microphone's diaphragm. The existence of two diaphragms, and the intervening air path, can result in excess ambient noise pickup by the microphone, as well as inefficient acoustic energy transfer. This inefficient acoustic energy transfer is a prevalent problem in the below-described electrical stethoscopes. Existing electronic stethoscopes use additional technologies to counteract this fundamentally inferior sensing technique, such as adaptive noise canceling and various mechanical isolation mountings for the microphone. However, these merely compensate for the inherent inadequacies of the acoustic-to-electrical transducers.

Piezo-electric sensors operate on a somewhat different principle than merely sensing diaphragm sound pressure. Piezo-electric sensors produce electrical energy by deformation of a crystal substance. In one case, the diaphragm motion deforms a piezoelectric sensor crystal mechanically coupled to the stethoscope diaphragm, resulting in an electrical signal. The problem with this sensor is that the conversion mechanism can produce signal distortion compared with sensing the pure motion of the diaphragm. The resulting sound is thus somewhat different in tone, and distorted compared with an acoustic stethoscope.

Capacitive acoustic sensors are in common use in high-performance microphones and hydrophones. A capacitive microphone utilizes the variable capacitance produced by a vibrating capacitive plate to perform acoustic-to-electrical conversion. A capacitive microphone placed behind a stethoscope diaphragm would suffer from the same ambient noise and energy transfer problems that occur with any other microphone mounted behind a stethoscope diaphragm.

Acoustic-to-electrical transducers operate on a capacitance-to-electrical conversion principle detecting diaphragm movement directly, converting the diaphragm movement to an electrical signal which is a measure of the diaphragm motion. Further amplification or processing of the electrical signal facilitates the production of an amplified sound with characteristics very closely resembling the acoustic stethoscope sound, but with increased amplification, while maintaining low distortion.

This is a significant improvement over the more indirect diaphragm sound sensing produced by the microphonic or piezoelectric approaches described above. Since the diaphragm motion is sensed directly, the sensor is less sensitive to outside noise, and the signal is a more accurate measure of the diaphragm movement. With an acoustic stethoscope, diaphragm movement produces the acoustic pressure waves sensed by the listener's ears. With an acoustic-to-electrical sensor, that same diaphragm movement produces the electrical signal in a direct manner. The signal is used to drive an acoustic output transducer such as earphones or headphones, to set up the same acoustic pressure waves impinging on the listener's ears.

While acoustic-to-electrical transducers overcome many of the inherent problems faced by earlier stethoscope designs, it adds considerable white noise to the signal. White noise is a sound that contains every frequency within the range of human hearing (generally from 20 hertz to 20 kHz) in equal amounts. Most people perceive this sound as having more high-frequency content than low, but this is not the case. This perception occurs because each successive octave has twice as many frequencies as the one preceding it. For example, from 100 Hz to 200 Hz, there are one hundred discrete frequencies. In the next octave (from 200 Hz to 400 Hz), there are two hundred frequencies.

As a result, the listener has difficulty discerning the human body sound from the white noise. For sounds of the body with higher intensities (i.e., louder sounds) the listener can hear the body sounds well, but lower-intensity sounds disappear into the background white noise.

In some instances, remote sensing technologies described above, such as UWB or capacitive sensor systems may be used to acquire vibro-acoustic data.

Kinesthetic Analysis

In certain embodiments, the sensor or the system includes a machine vision system comprising one or more cameras for capturing the motion of the subject as they stand or move (e.g. walking, running, playing a sport, balancing etc). In this manner, physiological states that affect kinesthetic movements such as balance and gait patterns, tremors, swaying or favoring a body part can be detected and correlated with the other data obtained from the other sensors in the apparatus such as center of mass positioning.

A wide range of motion analysis systems allow movement to be captured in a variety of settings, which can broadly be categorized into direct (devices affixed to the body, e.g. accelerometry) and indirect (vision-based, e.g. video or optoelectronic) techniques. Direct methods allow kinematic information to be captured in diverse environments. For example, inertial sensors have been used as tools to provide insight into the execution of various movements (walking gait, discus, dressage and swimming). Sensor drift, which influences the accuracy of inertial sensor data, can be reduced during processing; however, this is yet to be fully resolved and capture periods remain limited. Additionally, it has been recognized that motion analysis systems for biomechanical applications should fulfil the following criteria: they should be capable of collecting accurate kinematic information, ideally in a timely manner, without encumbering the performer or influencing their natural movement. As such, indirect techniques can be distinguished as more appropriate in many settings compared with direct methods, as data are captured remotely from the participant imparting minimal interference to their movement. Indirect methods were also the only possible approach for biomechanical analyses previously conducted during sports competition. Over the past few decades, the indirect, vision-based methods available to biomechanists have dramatically progressed towards more accurate, automated systems. However, there is yet to be a tool developed which entirely satisfies the aforementioned important attributes of motion analysis systems.

Thus, these analyses may be used in coaching and physical therapy in dancing, running, tennis, golf, archery, shooting biomechanics and other sporting and physical activities.

Other uses include ergonomic training for occupations that subject persons to the dangers of repetitive stress disorders and other physical stressors related to motion and posture. The data can also be used in the design of furniture, self-training, tools, and equipment design.

In one embodiment, the current technology comprises a multi-sensor information fusion platform for sensor integration. The selection of the platform first drives the decision of which combined outputs of what different sensor systems are required to obtain globally unique uDIDt-VeCx metrics according to set fusion rules. Multi-sensor fusion techniques refers to the combination of the features extracted from data of different modalities and decisions generated from these characteristics by classification algorithms. In one embodiment, the current technology comprises multi-sensor fusion where the information-flow spans raw sensor data, processing, segmentation, feature extraction, training and classification. In another embodiment, the current technology comprises sampling raw data from a plurality of sensors and generating a multivariable time series from the data.

In another embodiment, the current technology comprises the data fusion and data processing steps applying different algorithms to the raw data coming from the sensors to achieve time-synchronization between multimode sensor data, reduce the corruption of unprocessed sensor data, and leave the data ready for the extraction of features. In the data segmentation step the data is split into segments of desired length. In the fourth step, the characteristics of the segmented data are extracted and organized into group vectors that together describe data characteristics of interest.

Automatic grouping of characteristics allows the selection of data features with assigned meaning, which in turn allows the reduction of data into patterns to reduce computational needs. Traditional off-the-shelf ML models like neural nets or decision trees would follow segmentation and feature extraction with a training step. Contrary to typical ML scenarios with clearly delineated training and test phases, the current technology implements learning and optimizing software "inline". In another embodiment, the current technology embeds an 'inline learning' algorithm within the software system, allowing it to learn adaptively as the system processes new data within and between subjects. Such adaptation typically leads to a more performant software systems, that can (i) correct for the suboptimal biases introduced by humans unsupported by data, and (ii) respond swiftly to changing characteristics, context, and operating conditions (mostly driven by increase/decrease in variation in within- and between individual data being harvested).

In certain embodiments, the current technology provides methods and systems that implement multiple interacting domain specific languages that help explore and derive candidate contextualized vocabularies from collections of biometric data streams. In another embodiment, these vocabularies and themes are extracted to enable a meshed data network to learn and optimize unique globally identifiers while raw data are securely protected. In still another embodiment, accordance with social and regulatory concerns about privacy is achieved by not pooling participants' data. Rather, the current technology employs cryptography-motivated methods of 'differential privacy', which give formal guarantees of security and privacy on data shared over the meshed network.

Key attributes of the technology described herein's hardware/software platform include: 1) There's no need to ever pool data from multiple subjects, 2) No subject-specific measurements are ever permanently stored on the device, 3) All processing in the ML/AI pipeline is fully in-line and at the edge, 4) Time-synchronized data streams are ingested and processed on the fly, 5) Raw data on pre-existing participants/patients/subjects is not required (in the sense of https://en.wikipedia.org/wiki/Case-based_reasoning), and/or 6) The short 5-to-10 second time series biosignature phrase collected for each individual is not be stored in its entirety—the data is 'parsed' on the fly and evidence gradually accumulated during the four basic CRUD operations (create, read, update, deactivate) on the metadata associated with a uDIDt-VeCx.

Domain-specific terms provide vital semantic information for many natural language processing tasks and applications. An automatic domain-specific term extraction platform is used for signal processing and categorization/classification of biosignatures. The main properties utilized in the domain specific language approach is domain specificity. The notion of domain specificity is based on statistical frequency (TF) and inverse domain frequency (IDF) to capture feature specificity. The basic underlying idea is that domain-specific terms are extracted as informative features in a particular domain with markedly higher frequency than they do in other domains, similar to term frequency patterns captured by TF-IDF in language applications. The current technology's unsupervised methods have the advantage that they circumvent the need for laborious manual classification of training instances, and are thus readily applicable to arbitrary sets of biosignal data streams.

For example, vibroacoustic data can be characterized by pitch, timbre and timing of audible and inaudible sound signatures. These features can be extracted from individual subject data streams as well as across multiple individuals sharing the same or different diseases. Multiple turns of extracting pitch, timber and activation features reduces the necessary data required for accurate re-identification of individuals within a mixed cohort with high sensitivity and high specificity. Sensitivity and specificity may be increased by additional features such as harmonics (characteristic frequency bands), beat count, etc.

This section provides a basic understanding of the major elements of uDIDt-VeCx architecture.

uDIDt-VeCx and uDIDt-VeCx URLs

In one embodiment, a uDIDt-VeCx, or Decentralized Identifier, is a URL composed of three parts. In another embodiment, the scheme "udidtvecx:", a method identifier, and a unique, method-specific identifier are generated by the uDIDt-VeCx method. In still another embodiment, uDIDt-VeCx are resolvable to uDIDt-VeCx documents.

A uDIDt-VeCx URL extends the syntax of a basic uDIDt-VeCx to incorporate other standard URI components (path, query, fragment) in order to locate a particular resource—for example, a public key inside a uDIDt-VeCx document, or a resource available external to the uDIDt-VeCx document.

uDIDt-VeCx Subjects

The subject of a uDIDt-VeCx is, by definition, the entity identified by the uDIDt-VeCx. The uDIDt-VeCx subject may also be the uDIDt-VeCx controller.

In one embodiment, any member or members of a set comprising a person, community, group, organization, physical thing, or logical thing can be the subject of a uDIDt-VeCx.

uDIDt-VeCx Controllers

In another embodiment, the controller of a uDIDt-VeCx is the entity (person, organization, or autonomous software) that has the capability—as defined by a uDIDt-VeCx method—to make changes to a uDIDt-VeCx document. This capability is typically asserted by the control of a set of cryptographic keys used by software acting on behalf of the controller, though it may also be asserted via other mechanisms. In another embodiment, a uDIDt-VeCx may only have than one controller, while derivative uDIDts and VeCx may have more than one controller. In still another embodiment, the controller(s) may include the uDIDt-VeCx subject.

Verifiable Data Registries

In order to be resolvable to uDIDt-VeCx documents, uDIDt-VeCx are captured on an underlying verifiable bio-signature data registry.

uDIDt-VeCx Documents uDIDt-VeCx documents contain metadata associated with a uDIDt-VeCx. They typically express verification methods (such as validation/verification keys) and services relevant to interactions with the uDIDt-VeCx subject. In one embodiment, a uDIDt-VeCx document is serialized according to a particular syntax. In another embodiment, the uDIDt-VeCx itself is the value of the id property. In still another embodiment, the properties present in a uDIDt-VeCx document may be updated.

uDIDt-VeCx Methods

In one embodiment, uDIDt-VeCx methods are the mechanism by which a particular type of uDIDt-VeCx and its associated uDIDt-VeCx document are created, resolved, updated, and deactivated using a particular verifiable data registry.

uDIDt-VeCx Resolvers and uDIDt-VeCx Resolution

In one embodiment, a uDIDt-VeCx resolver is a software and/or hardware component that takes a uDIDt-VeCx (and associated input metadata) as input and produces a conforming uDIDt-VeCx document (and associated metadata) as output. This process is called uDIDt-VeCx resolution. In another embodiment, the specific steps for resolving a specific type of uDIDt-VeCx are defined by the relevant uDIDt-VeCx method specification.

uDIDt-VeCx URL Dereferencers and DID URL Dereferencing

In an embodiment, a uDIDt-VeCx URL dereferencer is a software and/or hardware component that takes a uDIDt-VeCx URL (and associated input metadata) as input and produces a resource (and associated metadata) as output. This process is called uDIDt-VeCx URL dereferencing.

In another embodiment, a conforming producer is any algorithm realized as software and/or hardware and conforms to this specification if it generates conforming uDIDt-VeCx or conforming uDIDt-VeCx Documents.

In still another embodiment, a conforming consumer is any algorithm realized as software and/or hardware and conforms to this specification if it consumes conforming uDIDt-VeCx or conforming uDIDt-VeCx documents.

In another embodiment, a conforming consumer MUST produce errors when consuming non-conforming uDIDt-VeCx or uDIDt-VeCx documents.

uDIDt-VeCx Keys

In one embodiment, a uDIDt-VeCx key is a verification method.

In another embodiment, uDIDt-VeCx keys are used for digital signatures, encryption and other cryptographic operations, which in turn are the basis for purposes such as authentication or establishing secure communication with service endpoints.

In still another embodiment, uDIDt-VeCx keys can play a role in authorization mechanisms of uDIDt-VeCx method operations, which can be defined by uDIDt-VeCx method specifications.

In an embodiment, uDIDt-VeCx keys can be included in a uDIDt-VeCx document using the uDIDt_VeCx key or authentication properties, depending on what they are to be used for.

In another embodiment, each uDIDt-VeCx key has properties for an identifier (id) of its own, a type, and a controller, as well as other properties that depend on the type of key it is.

Service Endpoints

Service endpoints are used in uDIDt-VeCx documents to express ways of communicating with the uDIDt-VeCx subject or associated entities.

In one embodiment, services listed in the uDIDt-VeCx document can contain information about privacy preserving messaging services, or more public information, such as social media accounts, personal websites, and email addresses although this is discouraged.

In another embodiment, the metadata associated with services are often service-specific. For example, the metadata associated with an encrypted messaging service can express how to initiate the encrypted link before messaging begins.

In still another embodiment, pointers to services are expressed using the service property. Each service has its own id and type properties, as well as a serviceEndpoint property with a URI or a set of other properties describing the service.

One of the primary purposes of a uDIDt-VeCx document is to enable discovery of service endpoints.

In one embodiment, a service endpoint can be any type of service the uDIDt-VeCx subject wants to advertise, including decentralized identity management services for further discovery, authentication, authorization, or interaction. The service endpoint protocol is published in an open standard specification.

uDIDt-VeCx Created

A uDIDt-VeCx document includes a created property.

Create

The uDIDt-VeCx method specification specifies how a client creates a uDIDt-VeCx and its associated uDIDt-VeCx document on the verifiable data registry, including all cryptographic operations necessary to establish proof of control.

Read/Verify

The uDIDt-VeCx method specification specifies how a client uses a uDIDt-VeCx to request a uDIDt-VeCx document from the verifiable data registry, including how the client can verify the authenticity of the response.

Update

The uDIDt-VeCx method specification specifies how a client can update a uDIDt-VeCx document on the verifiable data registry, including all cryptographic operations necessary to establish proof of control, or state that updates are not possible.

In an embodiment, an update to a uDIDt-VeCx is any change, after creation, in the data used to produce a uDIDt- VeCx document. uDIDt-VeCx Method implementers are responsible for defining what constitutes an update, and what properties of the uDIDt-VeCx document are supported by a given uDIDt-VeCx method. For example, an update operation which replaces key material without changing it could be a valid update that does not result in changes to the uDIDt-VeCx document.

Deactivate

In one embodiment, the uDIDt-VeCx method specification MUST specify how a client can deactivate a uDIDt-VeCx on the verifiable data registry, including all cryptographic operations necessary to establish proof of deactivation, or state that deactivation is not possible.

Authentication and Verifiable Claims

In one embodiment, a uDIDt-VeCx and uDIDt-VeCx document do not carry any PII (personally-identifiable information). The process of binding a uDIDt-VeCx to something in the real world, such as a person or a company, for example biosignature credentials with the same subject as that uDIDt-VeCx, is encompassed in the bring-your-own hardware handshake with biometric software of the current technology.

In another embodiment, the handshake enables transactions with matching software of the service endpoint provider, subject, or requesting party complying with the requirements of the authentication protocols supported at the service endpoint.

Notification of uDIDt-VeCx Document Changes

In one embodiment, as a mitigation against unauthorized changes to a uDIDt-VeCx document, the document is monitored continuously with actively notifying the uDIDt-VeCx subject when there are changes. This is analogous to preventing account takeover on conventional username/password accounts by sending password reset notifications to the email addresses on file.

In the case of a uDIDt-VeCx, there is no intermediary registrar or account provider to generate such notifications. However, if the verifiable data registry on which the uDIDt-VeCx is registered directly supports change notifications, a subscription service can be offered to uDIDt-VeCx controllers.

Key and Signature Expiration

In the proposed uDIDt-VeCx decentralized identifier architecture, the uDIDt-VeCx does not expire and there are no centralized authorities to enforce key or signature expiration policies. In one embodiment, the uDIDt-VeCx resolvers and other client applications need only validate that keys at the time they were used as expiration dates are moot.

Immutability

Many cybersecurity abuses hinge on exploiting gaps between reality and the assumptions of rational, good-faith actors. Like any ecosystem, the uDIDt-VeCx ecosystem has some potential for this to occur, however the likelihood is much reduced by the requirement of biosignature data. Because this biosignature specification is focused on both the creation of the uDIDt-VeCx itself as well as a data model instead of a protocol, it offers no opinion about many aspects of how that model is put to use. However, individual uDIDt-VeCx methods might want to consider constraints that would eliminate behaviors or semantics they do not need. The more locked down a uDIDt-VeCx method is, while providing the same set of features, the less it can be manipulated by malicious actors.

The notion that immutability provides some cybersecurity benefits is particularly relevant because of caching. For uDIDt-VeCx methods tied to a global source of truth, a direct, just-in-time lookup of the latest version of a uDIDt- VeCx document is always possible. However, it seems likely that layers of cache might eventually sit between a client and that source of truth. If they do, believing the attributes of an object in the uDIDt-VeCx document to have a given state, when they are actually subtly different, might invite exploits. This is particularly true if some lookups are of a full uDIDt-VeCx document, and others are of partial data, where the larger context is assumed.

uDIDt-VeCx Correlation Risks and Pseudonymous DIDs

Like any type of globally unique identifier, uDIDt-VeCx might be used for correlation. uDIDt-VeCx controllers can mitigate this privacy risk by using pairwise unique uDIDt-VeCx, that is, sharing a different derivative private uDIDt and VeCx for every relationship. In effect, each spawned uDIDt and VeCx pair acts as a pseudonym. A pseudonymous uDIDt-VeCx need only be shared with more than one party when the uDIDt-VeCx subject explicitly authorizes correlation between those parties. If pseudonymous uDIDt-VeCx are the default, then the only need for a public uDIDt-VeCx (a uDIDt-VeCx published openly or shared with a large number of parties) is when the uDIDt-VeCx subject explicitly desires public identification.

uDIDt-VeCx Document Correlation Risks

The anti-correlation protections of pseudonymous uDIDt-VeCx are easily defeated if the data in the corresponding uDIDt-VeCx documents can be correlated.

In one embodiment, the uDIDt-VeCx document for a pseudonymous uDIDt-VeCx also needs to use pairwise unique uDIDt-VeCx keys.

In another embodiment, endpoint privacy is increased by sharing factrorial outcomes of all uDIDt-VeCx and pseudonymous uDIDt and VeCx pairs endpoints among millions/billions of uDIDt-VeCx controlled by many different subjects.

Herd Privacy

When a uDIDt-VeCx subject is indistinguishable from others in the herd, privacy is available. When the act of engaging privately with another party is by itself a recognizable flag, privacy is greatly diminished. uDIDt-VeCx and uDIDt and VeCx pair pseudonymization methods improve herd privacy. (Objective quantitative sentiment metering in sports and tv, training)

Methods for Generating a Unique Identifier

In certain aspects, there is provided a method for generating a unique identifier for a subject. In one or more aspects, the method or one or more steps thereof may be performed by a computing system, such as the computing system 20 or the computing environment 100. The method or one or more steps thereof may be embodied in computer-executable instructions that are stored in a computer-readable medium, such as a non-transitory mass storage device, loaded into memory and executed by a CPU. The method is exemplary, and it should be understood that some steps or portions of steps in the flow diagram may be omitted and/or changed in order.

The method may comprise generating a unique identifier for a subject. The method may be executable by a processor of a computer system. The method may comprise: obtaining biometric data relating to the subject. The biometric data may be obtained using sensors, which may be proprietary sensors, such as passive vibroacoustic (analog voice-coil transducer), active vibrometry (pulse/continuous Doppler ultrasound), electric potential sensor (ultra-high, input impedance sensor that acts as a highly stable, extremely sensitive, contactless digital voltmeter to measure tiny changes in the electric field down to milliVolts), external data from other digital biometric data; all contextualized by environmental determinants data (GPS, elevation, humidity, Barometric pressure, ambient temperature, ambient light, ambient noise, etc). Current, past and future biometric data are consumed in a living biometric knowledge graph. Unlike traditional databases, which arrange data in rows, columns and tables, the biometric knowledge graph has a flexible evolutionary graph structure that stores not only the discreet biometric data but also the temporal, state and status relationships between biometric data records. Temporal in this case refers to longitudinal time stamps aligned with biometric data. State refers to the entire state of the biometric data lattice—all its values and relationships at a particular point in time or a single biometric data point across all time (usually, current), and status—biometric data at a point in time during a process or workflow—e.g., is it pending input, partial (in process), or complete, etc.

Because the biometric data knowledge graph is optimized for biometric data relationships, complex datasets are orders of magnitude faster and deeper than those of other databases including modern NoSQL flavors. Furthermore, inline learning is embedded methods which both enforce a partial order or lattice structure over the concept space, learn based from individuals and across individuals using structural machine learning algorithms which have unlimited expressiveness of queries and the ability to use uncertainty for both prediction and learning (e.g. learning from expectations) that have the ability to calibrate denotational probabilities while retaining the consistency and inductive bias of ordered models in an unbounded multi-biometric data relational lattice with rich joint and conditional queries over arbitrary sets of concepts for both learning from and predicting calibrated uncertainty to generate causally disentangled biometric biosignature representations Identification markers may be extracted from the biometric data. Biometrics provide an automated method of recognizing a person, similar in principle to discriminating between individuals by fingerprint or behavioral characteristics, such as handwriting. However, biosignature biometric identification relies on subtle large data measurements related physiological characteristics such as the iris, face, voice, cough, heart and breath rhythms. Our biometric measurements are primarily driven by vital sign measurements of the cardiopulmonary system. Specialized equipment can capture the full spectrum of electrical field and vibrations generated by the gut, lung, heart, and head. Our algorithms then select various invisible and visible light and audible and inaudible sound signals related to the movement of air and fluid movement in the body. Fluid and airflow parameters such as length, power, volume, acceleration, and variance that carry differentiating information between individuals are identified from training structural machine learning algorithms.

In outline, the novel algorithm used in the process described herein may involves a three stage pipeline. Stage 1: Training to identify, rank order and extract Extract Raw features of importance from each biometric data measurement (vibroacoustic, vibrometry, electric potential, context (environmental determinants), other biometric devices or data. Stage 2: Construct ensembles of raw features, into relational feature lattices. Stage 3: Leverage atom (individual) and ecology (population) inline learning to transform sized-for-use (minimal sized for edge inference computational efficiency) feature ensembles specific for the desired 1) "verifiable credential", 2) proof of "access control" attributes related to "verifiable credential", or 3) (classification, clustering, individuation etc. delivery of "conditional access" by extending "verifiable credential", and "access control" primitives with "temporal, state, and/or status biometrics." These stages may be performed sequentially, or in an overlapping (concurrent) manner as required to provide the required algorithmic performance.

The unique identifier may be generated from the extracted identification markers. Generating the unique identifier may comprise identifying a given domain specific feature which has predetermined identity compared to other domain specific features. In the real-world, information available about individuals is typically fragmentary and partial (represented in Stage 1 as isolated vibroacoustic, vibrometry, electric potential biometric information). In this sense, the nodes in the identification lattice can be considered to be analogous to individual pieces in a jigsaw puzzle: each has a number of specific inputs and outputs that only 'interlock' with compatible nodes. It is the task of the learning algorithm to impute missing data values in a consistent manner, which is analogous to synthesizing new compatible-jigsaw pieces. The Stage 2 overall learning task is to both identify an optimally small fragment of the overall jigsaw as to be able to yield an identifier with very low collision probability.

How the Knowledge Graph is Maintained

When new longitudinal data points are added, the embedded learning algorithms are invoked. This may change the compatibility of the associated 'jigsaw pieces' that they synthesise, which may in turn lead to a cascade of readjustment and resynthesis until a sufficiently consistent jigsaw fragment is again obtained.

How the Unique Biosignature is Validated at Point of Operation while being Optimized for Time and Accuracy The biosignature plays a role which is analogous to that of the 'public key' in RSA-style cryptosystems. Ensuring that validation at the point of operation is both computationally inexpensive and accurate (low collision probability) is part of the quality criteria for the embedded learning algorithms which generate the biosignature.

In certain aspects, there is provided a method for generating a unique identifier for a subject. In one or more aspects, the method or one or more steps thereof may be performed by a computing system, such as the computing system 20 or the computing environment 100. The method or one or more steps thereof may be embodied in computer-executable instructions that are stored in a computer-readable medium, such as a non-transitory mass storage device, loaded into memory and executed by a CPU. The method is exemplary, and it should be understood that some steps or portions of steps in the flow diagram may be omitted and/or changed in order.

The method comprises the following, in certain embodiments: A method for generating a unique identifier for a subject, the method executable by a processor of a computer system, the method comprising: obtaining biometric data relating to the subject; extracting identification markers from the biometric data; generating the unique identifier from the extracted identification markers, wherein the generating the unique identifier comprises identifying a given domain specific feature which has predetermined identity compared to other domain specific features.

EXAMPLE

Example 1

A Simple Example of a Decentralized Identifier (uDIDt-VeCx)

A uDIDt-VeCx is a simple text string consisting of three parts, the:

URL scheme identifier (udidt-vecx)

Identifier for the uDIDt-VeCx method uDIDt-VeCx method-specific identifier.

udidt_vecx: example: abcdefghijklm-nopqrstuvwxyz1234567890

The example uDIDt above resolves to a uDIDt-VeCx document. A uDIDt-VeCx document contains information associated with the uDIDt-VeCx, such as ways to cryptographically authenticate the uDIDt-VeCx controller, as well as services that can be used to interact with the uDIDt-VeCx subject.

FIG. 15 is a flow diagram of a method 1500 for authenticating an individual in accordance with various embodiments of the present technology. In one or more aspects, the method 1500 or one or more steps thereof may be performed by a computing system, such as the computing environment 100. The method 1500 or one or more steps thereof may be embodied in computer-executable instructions that are stored in a computer-readable medium, such as a non-transitory mass storage device, loaded into memory and executed by a CPU. Some steps or portions of steps in the flow diagram may be omitted or changed in order.

At step 1505 an individual's ID code may be scanned. Any identifier of the individual may be received at this step, such as a scan of a bar code or 3D bar code corresponding to the individual such as a QR code, a username of the individual, a name of the individual. The identifier may be received through a contactless interface, such as by scanning an RFID or other wireless chip corresponding to the individual, such as a chip integrated in an ID card of the individual. Any method of identifying an individual may be used. If the authentication is being performed on a device associated with an individual, such as a device the individual owns, the identifier of the individual may be selected by default without receiving further input.

At step 1510 a profile of the individual may be retrieved. The profile of the individual may be a uDIDt-VeCx as described above. The profile of the individual may include stored data describing the individual, such as vibroacoustic measurements of the individual, electric potential measurements of the individual, data describing physical and/or physiological characteristics of the individual, and/or any other data regarding the individual. The profile may include a history of data collected from the individual, such as data gathered during an initial profile creation and/or data captured when the individual authenticates themselves. Individual measurements stored in the profile may have associated data, such as associated data describing environmental conditions corresponding to the data collection. For example, the profile may have multiple stored heart rate measurements of the individual, and for each stored heart rate measurement a corresponding air temperature recorded at the time that the heart rate measurement was taken may be stored and associated with the heart rate measurement.

The profile of the individual may include any number of features corresponding to the individual. Each feature may be generated based on various input parameters. Various transformations may be applied to the input parameters, such as filters and/or mathematical operations. The features may be stored in the format of a numerical value and/or a vector.

Features may be generated using the following set of steps: 1) extracting raw features, 2) constructing ensembles of raw features, and 3) leveraging inline learning to generate feature ensembles specific to a particular use case.

Raw features may be extracted from each biometric data measurement, such as vibroacoustic, vibrometry, electric potential, context (environmental determinants), other biometric devices or data. These raw features may then be constructed into ensembles of raw features, which may be stored as relational feature lattices. Atom (individual) and ecology (population) inline learning may be used to transform sized-for-use (minimal sized for edge inference computational efficiency) feature ensembles specific for a desired use, such as 1) a verifiable credential, 2) proof of "access control" attributes related to the "verifiable credential", or 3) delivery of "conditional access" by extending "verifiable credential" and "access control" primitives with "temporal, state, and/or status biometrics."

Current, past, and future biometric data of the individual may be stored in a living biometric knowledge graph. This data may comprise the individual's profile. Unlike traditional databases, which arrange data in rows, columns and tables, the biometric knowledge graph may have a flexible evolutionary graph structure that stores not only the discreet biometric data but also the temporal, state and status relationships between biometric data records. Temporal in this case refers to longitudinal time stamps aligned with biometric data. State refers to the entire state of the biometric data lattice—all its values and relationships at a particular point in time or a single biometric data point across all time (usually, current), and status—biometric data at a point in time during a process or workflow—eg, is it pending input, partial (in process), or complete, etc.

Steps 1505 and/or 1510 are optional. A user profile may be retrieved at steps 1505 and 1510 and then a determination may be made as to whether the individual matches the user profile may be made using the steps of the method 1500 described below. But in other instances, the user profile might not be retrieved. Rather, the method 1500 may begin at step 1515 and an individual may be matched to a user profile based on a scan of the individual alone rather than based on the scan of the individual and an ID code (or other identifier) of the individual.

At step 1515 the individual may be scanned using a sensor array. The sensor array may include one or more sensors, such as a vibroacoustic sensor. The sensory array may contain a same set of sensors as the array used to collect data when generating the individual's user profile. The sensor array may include one or more cameras, vibroacoustic sensors, volatile organic compound sensors, wide frequency bandwidth terahertz sensors, microphones, altitude sensors, temperature sensors, barometric pressure sensors, air quality sensors, passive vibroacoustic sensors (analog voice-coil transducer), active vibrometry sensors (pulse/continuous Doppler ultrasound), electric potential sensors (ultra-high, input impedance sensor that acts as a highly stable, extremely sensitive, contactless digital voltmeter to measure tiny changes in the electric field down to milliVolts) and/or any other type of sensors. External data may also be collected from other digital biometric data The data collected at step 1515 may be contextualized by environmental determinants data (GPS, elevation, humidity, Barometric pressure, ambient temperature, ambient light, ambient noise, etc.) which may also be collected.

The sensor array may be a contactless sensor array, where the individual can be scanned without coming into physical contact with the sensor array. The sensor array may measure various characteristics of the individual and/or the environment surrounding the individual. The data may be captured over any period of time. The period of time may be predetermined and/or determined based on the collected data.

For example the individual's heart rate may be determined, and the data may be collected over a pre-determined number of heart beats.

At step 1520 a ranked list of features may be retrieved. The ranked list of features may have been generated using a machine learning algorithm (MLA). The ranked list of features may rank each of the available features. The features may be ranked based on how well each individual feature discriminates between individuals. Other criteria may be used for ranking the features in addition to and/or instead of how well individual features discriminate, such as how quickly an individual feature can be generated and/or how many resources are needed to generate an individual feature. For example a first feature that can be generated using very minimal resources and/or very quickly may be ranked more highly than a second feature that uses more resources to generate and/or takes longer to generate, even if the second feature is better at discriminating between individuals than the first feature.

At step 1525 the data collected at step 1515 may be converted to feature values. All or a portion of the features generated when creating the user profile may be generated at step 1520. Rather than generating all of the available features, it may be more efficient to generate a subset of the features. The data may be converted to feature values based on the rankings of the ranked list retrieved at step 1520. The feature value corresponding to the highest ranked feature in the ordered list may be determined first, the feature value corresponding to the next-highest ranked feature may be determined second, etc. A pre-determined number of feature values may be generated initially, such as the five highest-ranked features on the ordered list.

At step 1530 an initial set of potential matches for the data collected at step 1515 may be determined. The initial set of matches may be all of the user profiles in a database. For example if the individual is authenticating themselves at their workplace, the initial set of potential matches may be the profiles of all employees at the workplace.

At step 1535 a next feature in the ranked list of features may be selected. Initially, this would be the highest-ranked feature in the ranked list of features.

At step 1540 the feature value of the individual corresponding to the feature selected at step 1535 may be retrieved and/or determined. The feature value may have been previously determined at step 1525. An amount of error corresponding to the feature may be retrieved and/or determined. The amount of error may have been previously determined. The amount of error may be determined based on environmental measurements taken at step 1515. For example if the variability of a feature value is directly related to the ambient temperature, the amount of error may be determined based on the ambient temperature measured at step 1515.

Individuals that match the feature value and/or fall within the amount of error may be determined from the set of potential matches retrieved at step 1530. For example if the feature value of the individual for a specific feature is '0.075' and the amount of error is '0.005', a list of all profiles having measurements for that feature ranging from '0.070' to '0.080' may be retrieved.

A determination may be made at step 1540 as to whether there is a unique match for the individual. If a single profile in the set of potential matches corresponds to the feature, than a unique match is obtained and the method 1500 may continue to step 1545. Otherwise, if there are multiple potential matches at step 1540, the method 1500 may continue to step 1560.

Although step 1540 describes finding a unique match for an individual, a threshold number of potential matches may be used at step 1540. The threshold may be a pre-determined threshold. For example, if the pre-determined threshold is five matches, the method 1500 may continue to step 1545 if there are five or less potential matches remaining at step 1540. Otherwise, if there are more than five potential matches remaining, the method 1500 may continue to step 1560.

Increasing the threshold number of matches to be used at step 1540 may cause the method 1500 to execute more quickly and/or use less resources. But the accuracy of the authentication may be decreased. The threshold number may be selected based on the application of the method 1500. For example, in a low security environment where speed is prioritized, the threshold number may be set to be very high. Conversely, for an application where security is key, such as for authenticating an individual so that they can retrieve secure information such as their medical records, or for authenticating an individual so that they can access funds from their bank, the threshold may be set to one (as illustrated in FIG. 15) to reduce the risk that an individual is incorrectly authenticated.

At step 1560, if a unique match has not been found yet and/or the number of potential matches is above the threshold, individuals that do not match the current feature may be removed from the set of potential matches. All profiles in the set of potential matches that are not within the error margin of the current feature value may be filtered out of the set of potential matches. In this manner, each time the method 1500 proceeds through the steps of 1535, 1540, and 1560 the set of potential matches may get smaller until only a single match remains (or the number of potential matches is less than the threshold number), at which point the method 1500 continues to step 1545.

At step 1545 a determination may be made as to whether the unique match remaining in the set of potential matches is a match to the profile determined at step 1510. In other words, does the profile corresponding to the individual's ID code match the scan of the individual. If there is a match, the method 1500 proceeds to step 1550 and the individual is authenticated. Otherwise, if there is not a match, the method 1500 proceeds to steps 1555 and there is an authentication fail.

If there is a set of profiles remaining at step 1545, rather than a single profile, a determination may be made as to whether the profile retrieved at step 1510 matches one of the profiles that remains in the set of potential matches. If the retrieved profile matches one of the remaining profiles, the individual may be authenticated at step 1550. Otherwise the authentication may fail at step 1555.

As described above, in some instances an ID code or other identifier of the individual might not be used. In that case, the method 1500 may proceed through the steps 1535, 1540, and 1560 until a unique match is made. After a unique match is made, the method 1500 may proceed directly to step 1550 and the individual may be authenticated as the user profile corresponding to the unique match.

Figure 16:
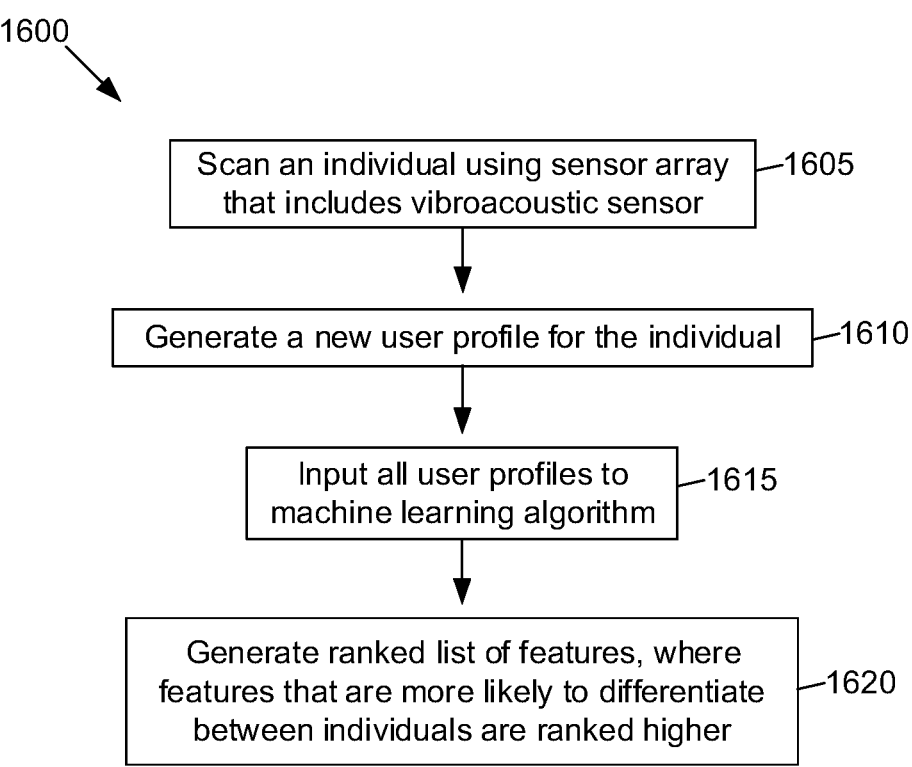
FIG. 16 is a flow diagram of a method for generating a profile of an individual in accordance with various embodiments of the present technology.

FIG. 16 is a flow diagram of a method 1600 for generating a profile of an individual in accordance with various embodiments of the present technology. In one or more aspects, the method 1600 or one or more steps thereof may be performed by a computing system, such as the computing environment 100. The method 1600 or one or more steps thereof may be embodied in computer-executable instructions that are stored in a computer-readable medium, such as a non-transitory mass storage device, loaded into memory and executed by a CPU. Some steps or portions of steps in the flow diagram may be omitted or changed in order.

At step 1605 an individual may be scanned using a sensor array. Actions performed at step 1605 may be similar to those described above with regard to step 1515 of the method 1500. In addition to measuring data of the individual, identifying data may be input manually and/or retrieved, such as a name of the individual, ID number of the individual, birth date of the individual, etc.

At step 1610 a user profile may be generated for the individual. Feature values may be generated for the individual. Various features may have been pre-determined. A function may be associated with each feature, where the function specifies what parameters measured at step 1605 are input to the function and how those parameters are processed. A feature value may be output by the function. The feature value may be a numerical value, a vector, and/or any other type of output. A set of available features may be retrieved, and feature values for the individual may be generated for all features in the set of available features or a subset of the features in the set of available features.

The user profile may be added to a database, such as a database stored in a cloud system. Prior to adding the user profile to the database, the user profile may be compared to all of the other profiles in the database to confirm that the profile is unique. If the profile is determined to be a duplicate of a previous profile, an error may be output, and the profile might not be added to the database.

At step 1615 all profiles of the database may be input to a machine learning algorithm (MLA). The profiles and/ feature values of the profiles may be input to the MLA. All feature values for a profile may be input to the MLA or a subset of the available feature values may be input to the MLA.

At step 1620 a ranked list of features may be generated by the MLA. The MLA may output a ranked list of features and/or a value corresponding to each feature. If the MLA outputs a value corresponding to each feature, the values may be used to rank the features and generate a ranked list. The value may indicate how likely each feature is to differentiate between individuals in the database. If a feature is highly likely to differentiate between individuals, the MLA may rank the feature relatively high. Conversely, if a feature is not likely to differentiate between individuals (such as if most individuals have a similar feature value for this feature), that feature may receive a relatively lower ranking. The ordered list of features may then be used to authenticate individuals, such as at step 1520 of the method 1500.

As described above, the user profiles may be stored in a knowledge graph-based structure. Because the biometric data knowledge graph is optimized for biometric data relationships, operations described herein may be executed orders of magnitude faster and deeper than those performed using other databases—including modern NoSQL databases. Furthermore, inline learning (generating the ranked list of features) may us embedded methods which both enforce a partial order or lattice structure over the concept space, learn based from individuals and across individuals using structural machine learning algorithms which may have unlimited expressiveness of queries and the ability to use uncertainty for both prediction and learning (e.g. learning from expectations) that have the ability to calibrate denotational probabilities while retaining the consistency and inductive bias of ordered models in an unbounded multi-biometric data relational lattice with rich joint and conditional queries over arbitrary sets of concepts for both learning from and predicting calibrated uncertainty to generate causally disentangled biometric biosignature representations Steps 1615 and 1620 may be performed to generate the ranked list of features each time a new user profile is added to the database, when a pre-determined amount of new user profiles are added to the database, at a predetermined time interval, and/or based on any other trigger.

The invention claimed is:

1. A method for generating a unique algebraic lattice identifier for a subject, the method executable by a processor of a computer system, the method comprising:
   obtaining biometric data relating to the subject from a vibroacoustic sensor having a bandwidth ranging from 0.01 Hz to 160 kHz;
   extracting an identification marker from the biometric data comprising at least one of cross-frequency coupling and cross-phase coupling from the biometric data; and
   generating the unique algebraic lattice identifier from the extracted identification marker, wherein the generating the unique identifier comprises identifying a given domain specific feature having a predetermined identity compared to other domain specific features.

2. The method of claim 1, wherein the predetermined identity has a higher occurrence than other domain specific features, or comprises a higher frequency event than other domain specific features.

3. The method of claim 1, wherein the given domain specific feature is characterized based on one or more of a pitch, an amplitude, a peak, an area under the curve, a frequency, a spectral distribution, a total energy, a timbre, a timing, frequency bands, and harmonic distribution.

4. The method of claim 1, further comprising storing the generated unique identifier in a database of the processor.

5. The method of claim 1, wherein the generating the unique algebraic lattice identifier occurs at a first time point, the method further comprising, at a second time point which is later than or at the same time as the first time point, comparing the generated identifier with a reference identifier to determine a presence of predetermined common features.

6. The method of claim 1, further comprising one or more of:
   determining whether to accept the biometric data based on predetermined criteria;
   processing the biometric data to enhance a signal thereof;
   processing the biometric data to normalize a signal thereof, or processing the biometric data to perform evolutionary structural machine learning, signal aggregation and abstraction of a signal thereof.

7. The method of claim 1, wherein the obtaining the biometric data comprises a baseline phase and a base-line update phase, a data segment in the baseline phase being larger than a data segment in the base-line update phase.

8. The method of claim 1, wherein the obtaining the biometric data comprises acquiring data at sampling rates of about 0.01 Hz to about 20 THz.

9. The method of claim 1, further comprising adding a time stamp to the generated unique identifier.

10. The method of claim 1, further comprising obtaining input of an event related parameter and generating a status identifier incorporating information about the unique identifier and the event.

11. The method of claim 1, further comprising converting a bit output of the generated unique algebraic lattice identifier according to a bit requirement of another digital identification solution which has a different requirement.

12. The method of claim 1, further comprising obtaining input of an emotional/cognitive state of the subject, or a health state of the subject and incorporating with the generated unique algebraic lattice identifier.

13. The method of claim 1, further comprising use of the generated unique algebraic lattice identifier as one or more of a health state confirmation; emotional/cognitive feedback.

14. The method of claim 1, further comprising:

retrieving a profile corresponding to the subject;

obtaining current biometric data of the subject;

retrieving an ordered list of features;

generating, based on the biometric data, one or more feature values corresponding to highest-ranked features in the ordered list of features;

determining a user profile from a database of user profiles that matches the one or more feature values; and outputting an indication that the subject has been authenticated after determining that the user profile from the database matches the retrieved profile corresponding to the subject.

15. The method of claim 14, wherein the ordered list of features was generated by a machine learning algorithm (MLA) trained to rank features based on their ability to discriminate between individuals, wherein features that are more likely to discriminate between individuals are assigned a higher ranking in the ordered list of features.

16. The method of claim 14, wherein determining the user profile that matches the one or more feature values comprises:

iterating through the ordered list of features until a unique profile matching the biometric data of the subject is found, or iterating through the ordered list of features until an amount of potential matches for the biometric data of the subject is less than a predetermined threshold amount.

17. A system for generating a unique algebraic lattice identifier for a subject, the system comprising a processor of a computer system, the processor configured to execute a method, the method comprising:

obtaining biometric data relating to the subject from a vibroacoustic sensor having a bandwidth ranging from 0.01 Hz to 160 kHz;

extracting an identification marker from the biometric data comprising at least one of cross-frequency coupling and cross-phase coupling from the biometric data; and generating the unique algebraic lattice identifier from the extracted identification marker, wherein the generating the unique algebraic lattice identifier comprises identifying a given domain specific feature having a predetermined identity compared to other domain specific features.

18. The system of claim 17, further comprising the vibroacoustic sensor in a sensor array for obtaining the biometric data.

* * * * *